United States Patent
Ashley et al.

(10) Patent No.: US 10,283,781 B2
(45) Date of Patent: May 7, 2019

(54) LEWIS ACID ELECTROCATALYSED FUEL CELL AND BATTERY

(71) Applicant: UEA Enterprises Limited, Norwich, Norfolk (GB)

(72) Inventors: Andrew Edward Ashley, London (GB); Gregory Wildgoose, Norwich (GB); Elliot Lawrence, Norwich (GB)

(73) Assignee: UEA Enterprises Limited, Norwich Norfolk (GB)

( * ) Notice: Subject to any disclaimer, the term of this patent is extended or adjusted under 35 U.S.C. 154(b) by 156 days.

(21) Appl. No.: 15/116,911

(22) PCT Filed: Feb. 2, 2015

(86) PCT No.: PCT/EP2015/052088
§ 371 (c)(1),
(2) Date: Aug. 5, 2016

(87) PCT Pub. No.: WO2015/117923
PCT Pub. Date: Aug. 13, 2015

(65) Prior Publication Data
US 2017/0179499 A1    Jun. 22, 2017

(30) Foreign Application Priority Data
Feb. 5, 2014  (GB) .................... 1401981.4

(51) Int. Cl.
*H01M 4/00* (2006.01)
*H01M 4/90* (2006.01)
(Continued)

(52) U.S. Cl.
CPC .......... *H01M 4/9008* (2013.01); *C07F 5/027* (2013.01); *H01M 4/96* (2013.01); *H01M 8/08* (2013.01);
(Continued)

(58) Field of Classification Search
CPC ........... H01M 8/08; H01M 2300/0014; H01M 4/9008; C07F 5/027; C07F 5/06; C07F 9/00
See application file for complete search history.

(56) References Cited

U.S. PATENT DOCUMENTS 8,299,284 B2 * 10/2012 Stephan ............... B01J 31/0267
556/1
2010/0068594 A1 * 3/2010 Aihara .................. C08J 5/2256
429/446
2012/0115065 A1    5/2012 Hirakimoto et al.

FOREIGN PATENT DOCUMENTS

WO     2012/159818     11/2012
WO     2013/177708     12/2013
WO  WO 2013/177708  * 12/2013  ............... C07F 5/02

OTHER PUBLICATIONS

International Search Report for PCT/EP2015/052088 dated May 15, 2015.
(Continued)

*Primary Examiner* — Cynthia H Kelly
*Assistant Examiner* — Monique M Wills
(74) *Attorney, Agent, or Firm* — Honigman LLP; Andrew N. Weber; Jonathan P. O'Brien

(57) ABSTRACT

The present invention relates to the use of an electrocatalytic frustrated Lewis pair system in either an energy generation device such as a fuel cell or an energy storage device such as a battery or capacitor.

17 Claims, 11 Drawing Sheets

(51) Int. Cl.
- *H01M 8/08* (2016.01)
- *H01M 4/96* (2006.01)
- *C07F 5/02* (2006.01)

(52) U.S. Cl.
CPC ........... *H01M 2300/0014* (2013.01); *H01M 2300/0025* (2013.01)

(56) References Cited

OTHER PUBLICATIONS

Lawrence, Elliot J. et al., "A Combined "Electrochemical-Frustrated Lewis Pair" Approach to Hydrogen Activation: Surface Catalytic Effects at Platinum Electrodes", Chem. Eur. J., vol. 21, 2015, pp. 900-906.

Lawrence, Elliot J. et al., "Exploring the fate of the tris(pentafluorophenyl)borane radical anion in weakly coordinating solvents—Supporting Information Cyclic Voltammetry", Dalton Transactions, Nov. 22, 2012, whole document.

Lawrence, Elliot J. et al., "Exploring the fate of the tris(pentafluorophenyl)borane radical anion in weakly coordinating solvents", Dalton Transactions, vol. 42, No. 3, Nov. 22, 2012, pp. 782-789.

O C IE et al: "Book of Abstracts of the 13th Topical Meeting of the International Society of Electrochemistry: Practical Electrochemical Sensors with Relevance to Africa Organized by: ISE Division 4 Electrochemical Materials Science ISE Division 5 Electrochemical Process Engineering and Technology ISE Region South Africa", Apr. 11, 2013.

Ramos, Alberto et al., "Activation of H2 by frustrated Lewis pairs derived from mono- and bis-phosphinoferrocenes and B(C6F5)3" Chem. Commun., 2009, pp. 1118-1120.

Rokob, Tibor Andras et al., "Rationalizing the Reactivity of Frustrated Lewis Pairs: Thermodynamics of H2 Activation and the Role of Acid-Base Properties", Journal of the American Chemical Society, vol. 131, No. 30, Aug. 5, 2009, pp. 10701-10710.

Search Report for GB1401981.4 dated Aug. 4, 2014.

Stephan, Douglas W., "Frustrated Lewis pairs: a new strategy to small molecule activation and hydrogenation catalysis", Dalton Transactions, Royal Society of Chemistry, No. 17, May 7, 2009, pp. 3129-3136.

Sumerin, Victor, "Lewis Acid-Lewis Base Mediated Metal-Free Hydrogen Activation and Catalytic Hydrogenation", Oct. 14, 2011.

Welch, Gregory C. et al., "Reversible, Metal-Free Hydrogen Activation", Science, vol. 314, Nov. 17, 2006, pp. 1124-1126.

Wildgoose, Gregory G. et al. "Introducing "Electrocatalytic Frustrated Lewis Pairs" (e-FLP) for Hydrogen and Small Molecule Activation", Pretoria, 2013.

* cited by examiner

US 10,283,781 B2

LEWIS ACID ELECTROCATALYSED FUEL CELL AND BATTERY

CROSS REFERENCE TO RELATED APPLICATIONS

This U.S. nonprovisional application is the 35 USC § 371 national phase of PCT Application No. PCT/EP2015/052088, filed on Feb. 2, 2015, which claims the benefit of GB Application No. 1401981.4, filed on Feb. 5, 2014. Each of these documents is hereby incorporated by reference in its entirety.

TECHNICAL FIELD

The present invention generally relates to electrocatalysed fuel cells and rechargeable batteries. The present invention particularly relates to the electrocatalytic oxidation of hydrogen in hydrogen fuel cells and rechargeable hydrogen-batteries. The present invention more particularly relates to the use of aromatically substituted boron-containing Lewis acidic species to electrocatalytically oxidise hydrogen in electrocatalysed hydrogen fuel cells and rechargeable hydrogen-batteries.

BACKGROUND

There is an ever increasing demand for sustainable, clean and low-cost sources of electrical energy. Though predating the invention of the internal combustion engine, hydrogen fuel cell technology has faced several major obstacles that have prevented its mainstream adoption as an electricity and power source. The main obstacles preventing further implementation of fuel cells as a main power source include the expense of the required materials and the fragility and failure of the components making up the fuel cells.

Precious metals are conventionally used in aqueous hydrogen fuel cells as a catalytic electrode material to lower the overpotential required for hydrogen oxidation. For example, platinum can be used as a catalytic electrode material for both half-cell reactions of a hydrogen fuel cell (hydrogen oxidation and oxygen reduction). However, the expense and rarity of these metals has hindered the widespread adoption of hydrogen fuel cell technology. As a result, there have been many studies aimed at finding abundant, inexpensive alternative catalysts to precious metals that lower the overpotential required for hydrogen oxidation.

The majority of these studies have focused on the use of natural and synthetic hydrogenase enzymes with [FeFe] or [FeNi] metal-centred active sites having suitable pendant Lewis basic ligands in close proximity (for example P. M. Vignais et al; *Chem. Rev.* 2007, 107, 4206-4272). These enzymes are able to overcome the high level of energy required to heterolytically cleave hydrogen by virtue of the strong hydricity of the metal centre and the strong proton acceptors provided by the pendant Lewis base ligands.

Research has also been conducted into the use of molecular electrocatalysts containing nickel, iron, cobalt and molybdenum metal centres. Rauchfuss et al (M. R. Ringenberg et al; *J. Am. Chem. Soc.;* 2008, 130, 788-789) have provided an alternative approach to the electrocatalytic oxidation of hydrogen using unsaturated iridium complexes with redox-active non-innocent amidophenolate ligands.

All of these previous approaches still require a metal-containing catalyst and there is a prevalent research focus on enzymes and synthetic biomimetic electrocatalysts for proton reduction to generate hydrogen, rather than the oxidation of hydrogen. Thus far, the challenge of finding an inexpensive, metal-free method of oxidising hydrogen has not been solved by this area of research.

It is therefore an object of the present invention to provide a catalyst system for a fuel cell which can reduce the overpotential required for hydrogen oxidation without the need for expensive and fragile metal catalysts systems. For example, a fuel cell which reduces or removes the need for a precious metal or biomimetic metal-centred enzyme type catalysts would reduce the expense and also eliminate the risk of metal catalyst contamination or poison.

An alternative method of heterolytically cleaving hydrogen has been suggested by Stephan et al (G. C. Welch et al; *Science,* 2006, 314, 1124-1126). The method requires the presence of a sterically encumbered Lewis acid and Lewis base that are incapable of forming a classical Lewis adduct due to the hindrance of sterically bulky groups. The Lewis acid and Lewis base are said to form a frustrated Lewis pair (FLP) which, on the introduction of hydrogen into the system, is able to heterolytically cleave the hydrogen molecule to form a hydride of the Lewis acid and a protonated base.

It is known in the art that boranes can be used as the Lewis acid component and phosphines or amines can be used as the Lewis base component for the frustrated Lewis pair, although these components can be combined on the same molecule. Typically these components will comprise sterically bulky groups that hinder the formation of a dative covalent bond. Examples of such frustrated Lewis pairs include $^tBu_3P/B(C_6F_5)_3$, 2,2,6,6-tetramethylpiperidine/B$(C_6F_5)_3$ and $(Mes)_2P(C_6F_4)B(C_6F_5)_2$.

Known applications for frustrated Lewis pairs include their use as metal-free hydrogenation catalysts and also using the borane hydride adduct as activating or reducing agent for other small molecules such as imines, enamines, nitriles or $CO_2$.

A process for the catalytic hydrogenation of a variety of organic substrates using a frustrated Lewis pair catalyst is described in WO2013/177708 A1. The frustrated Lewis pair is a carbene stabilised borenium complex combined with a substituted amine or phosphine, which is used as a catalyst in chemical hydrogenation and reduction reactions.

In addition to the above uses, Stephan et al. (*Chem. Comm;* 2009, 1118) describes the use of a ferrocene redox label attached to an FLP to observe the reduction of the proton on FLP-activated mono- and bis-ferrocenylphosphines, in addition to observing the ferrocene signal itself.

However, there have been no investigations to date of the electrocatalytic behaviour of frustrated Lewis pairs or the tuning of these systems to create a clean and efficient source of energy from the heterolytic cleaving of dihydrogen ($H_2$). In addition, these frustrated Lewis pair systems have not been employed to reduce the overpotential required to oxidise hydrogen in hydrogen fuel cell applications.

DISCLOSURE OF THE INVENTION

The present invention is defined in the accompanying claims.

The present invention relates to the use of an electrocatalytic frustrated Lewis pair system in either an energy generation device such as a fuel cell or an energy storage device such as a battery or capacitor.

In power delivery, the frustrated Lewis pair heterolytically cleaves dihydrogen ($H_2$), resulting in the hydride of the Lewis acid and a protonated Lewis base. The resulting Lewis acid hydride can then be readily oxidised, generating a proton and two electrons, which can then be utilised in a fuel cell to generate electrical energy, together with the proton from the conjugate acid of the Lewis base.

Therefore, in accordance with the first aspect of the present invention there is provided a fuel cell comprising an anode and a cathode, the fuel cell being capable of operating in a power delivery mode in which it generates electrochemical power by the reaction of electrochemically active species at the anode; the fuel cell comprising;
  a Lewis acid (A),
  a Lewis base (B),
  and hydrogen;
wherein the electrochemically active species at the anode is the Lewis acid hydride formed via the heterolytic cleavage of dihydrogen ($H_2$) represented as;

$$H_2 + A + B \Longleftrightarrow AH^- + BH^+;$$

and wherein the redox reaction of the electrochemically active species at the anode when the fuel cell is in power delivery mode is;

$$AH^- \rightarrow A + H^+ + 2e^-.$$

In accordance with a second aspect of the present invention there is provided a method of electrocatalytically oxidising dihydrogen ($H_2$) using a Lewis acid, a Lewis base and at least one electrode; the method comprising the steps of:
  a. introducing dihydrogen to the Lewis acid and Lewis base;
  b. heterolytically cleaving dihydrogen to produce an electrochemically active Lewis acid hydride; and
  c. electrochemically oxidising the electrochemically active Lewis acid hydride.

In accordance with a third aspect of the present invention there is provided an electrode in combination with a Lewis acid according to any of the compounds as described herein, wherein the Lewis acid can form a hydride via the heterolytic cleavage of dihydrogen ($H_2$) using a Lewis base.

Definitions

In accordance with standard terminology in the field of chemistry, the following definitions are provided for reference only and, as such they should not be considered as limiting. The scientific and chemical terms used herein have their conventional meaning as would be understood by a person skilled in the art, unless otherwise defined.

The expression $pK_a$ has its conventional meaning as the acid dissociation constant to denote the strength of an acid, or the conjugate acid of a base, in solution. Typically the solvent is water or dimethyl sulfoxide (DMSO). The $pK_a$ of the acid species can be determined using a standard pH meter or spectrophotometric titration techniques.

The term alkyl has its conventional meaning and particularly refers to a straight chain or branched alkyl functional group, typically comprising at least one and up to six carbon atoms, specifically one, two, three, four, five or six. Examples of such alkyls include, but are not limited to, methyl, ethyl, propyl (n-propyl or isopropyl), butyl (n-butyl, sec-butyl or t-butyl), pentyl, and hexyl. Specifically, an alkyl may have at least one and up to four carbon atoms.

The term cycloalkyl has its conventional meaning and particularly refers to an aliphatic cyclic functional group having at least three and up to eight carbon atoms, specifically three, four, five, six, seven or eight. In addition, the functional group may be a bridged or a polycyclic ring system. Examples of such cycloalkyl functional groups include, but are not limited to, cyclopropyl, cyclobutyl, cyclopentyl and cyclohexyl. Specific examples of a bridging ring system include norbornyl and bicyclo[2.2.2]octyl.

The term alkoxy has its conventional meaning and particularly refers to —O-alkyl functional groups, wherein alkyl means a straight chain or branched alkyl functional group, typically comprising at least one and up to six carbon atoms, specifically one, two, three, four, five or six. Specifically, the preferred alkoxy groups have at least one and up to four carbon atoms. Examples of such alkoxy include, but are not limited to, methoxy, ethoxy, propoxy, isopropoxy, butoxy, t-butoxy, pentoxy, and hexoxy.

The term hydrocarbyl has its conventional meaning and particularly refers to typically aliphatic moieties consisting of at least one and up to twelve carbons atoms, specifically one, two, three, four, five, six, seven, eight, nine, ten, eleven or twelve. Examples of such hydrocarbyl groups include, but are not limited to, ($C_{1-6}$)alkyl (i.e. methyl, ethyl, propyl, isopropyl, n-butyl, sec-butyl or tert-butyl); ($C_{2-6}$)alkenyl (i.e. propenyl); and ($C_{2-6}$)alkynyl (i.e. propynyl).

The term fluorocarbyl has its conventional meaning and particularly refers to typically aliphatic moieties consisting of at least one and up to twelve carbons atoms, specifically one, two, three, four, five, six, seven, eight, nine, ten, eleven or twelve, which are substituted with fluorine. Examples of such fluorocarbyl groups include, but are not limited to, ($C_{1-6}$)fluoroalkyl (i.e. tri-fluoromethyl, penta-fluoroethyl, hepta-fluoropropyl, hepta-fluoroisopropyl, nona-fluoro-n-butyl, nona-fluoro-sec-butyl or nona-fluoro-tert-butyl); ($C_{2-6}$)fluoroalkenyl (i.e. penta-fluoropropenyl); and ($C_{2-6}$)fluoroalkynyl (i.e. fluoropropynyl).

The term chlorocarbyl has its conventional meaning and particularly refers to typically aliphatic moieties consisting of at least one and up to twelve carbons atoms, specifically one, two, three, four, five, six, seven, eight, nine, ten, eleven or twelve, which are substituted with chlorine. Examples of such chlorocarbyl groups include, but are not limited to, ($C_{1-6}$)chloroalkyl (i.e. tri-chloromethyl, penta-chloroethyl, hepta-chloropropyl, hepta-chloroisopropyl, nona-chloro-n-butyl, nona-chloro-sec-butyl or nona-chloro-tert-butyl); ($C_{2-6}$)chloroalkenyl (i.e. penta-chloropropenyl); and ($C_{2-6}$)chloroalkynyl (i.e. chloropropynyl).

The term chloro-fluorocarbyl has its conventional meaning and particularly refers to typically aliphatic moieties consisting of at least one and up to twelve carbons atoms, specifically one, two, three, four, five, six, seven, eight, nine, ten, eleven or twelve, which are partially or fully substituted with fluorine and chlorine. Examples of such chloro-fluorocarbyl groups include, but are not limited to, ($C_{1-6}$)chlorofluoroalkyl; ($C_{2-6}$) chloro-fluoroalkenyl; and ($C_{2-6}$) chlorofluoroalkynyl.

The term fluoro-hydrocarbyl has its conventional meaning and particularly refers to typically aliphatic moieties consisting of at least one and up to twelve carbons atoms, specifically one, two, three, four, five, six, seven, eight, nine, ten, eleven or twelve, which are partially substituted with fluorine. Examples of such fluoro-hydrocarbyl groups include, but are not limited to, ($C_{1-6}$) fluoro-hydroalkyl; ($C_{2-6}$) fluoro-hydroalkenyl; and ($C_{2-6}$) fluoro-hydroalkynyl.

The term chloro-hydrocarbyl has its conventional meaning and particularly refers to typically aliphatic moieties consisting of at least one and up to twelve carbons atoms, specifically one, two, three, four, five, six, seven, eight, nine, ten, eleven or twelve, which are partially substituted with chlorine. Examples of such chloro-hydrocarbyl groups include, but are not limited to, ($C_{1-6}$)chloro-hydroalkyl; ($C_{2-6}$) chloro-hydroalkenyl; and ($C_{2-6}$) chloro-hydroalkynyl.

The term aryl has its conventional meaning and particularly refers to an aromatic ring system comprising at least six and up to ten carbon atoms, specifically six, seven, eight, nine or ten. Typically aryl refers to phenyl but may also be a polycyclic ring system, at least two rings, with at least one of which being aromatic. Examples of aryl groups include, but are not limited to, phenyl, naphthyl and mesityl.

The term heteroaryl has its conventional meaning and particularly refers to an aromatic heterocyclic ring system comprising at least six and up to ten carbon atoms, specifically six, seven, eight, nine or ten, with at least one of the carbons replaced with a non-carbon atom, preferably selected from nitrogen, oxygen and sulphur. Typically heteroaryl refers to a single ring system but may also be a polycyclic ring system with at least two rings, with at least one ring being aromatic. Examples of such heteroaryl groups include, but are not limited to, benzo[b]thiophenyl, benzo[b]furanyl, benzimidazolyl, furanyl, imidazolyl indazolyl, indolyl, isoindolyl, isoxazolyl, isoquinolinyl, oxazolyl, phenothiazinyl, phthalazinyl, pteridinyl, purinyl, pyrazinyl, pyridinyl, pyrimidinyl, pyrrolyl, pyrrolidinyl, quinazolinyl, quinolinyl, thiazolyl, thiophenyl, and triazinyl.

The term carbocyclyl has its conventional meaning and particularly refers to a saturated or unsaturated ring functional group comprising at least three and up to ten carbon atoms in a ring configuration, specifically three, four, five, six, seven, eight, nine or ten. Specifically, the term carbocyclyl includes a saturated or unsaturated three to ten membered ring or ring system and, more specifically, a saturated or unsaturated six membered ring. Examples saturated carbocyclyl groups include, but are not limited to, cyclopropyl, cyclobutyl, cyclopentyl and cyclohexyl. Examples of bridging carbocyclyl groups include, but are not limited to, norbornyl and bicyclo[2.2.2]octyl. Examples of unsaturated carbocyclyl groups include, but are not limited to, phenyl and naphthyl.

The term heterocyclyl has its conventional meaning and particularly refers to a saturated (e.g. heterocycloalkyl) or unsaturated (e.g. heteroaryl) heterocyclic ring functional groups comprising at least three and up to ten carbon atoms in a ring configuration, with at least one of the carbons replaced with a non-carbon atoms, preferably selected from nitrogen, oxygen, phosphorous silicon and sulphur. Specifically, heterocyclyl refers to a saturated or unsaturated, five to ten membered ring or ring system and more specifically a saturated or unsaturated, five or six membered ring.

Examples of heterocyclic groups include, but are not limited to acridinyl, β-carbolinyl, benzofuranyl, benzothiophenyl, benzimidazolyl, carbazolyl, chromanyl, chromenyl, cinnolinyl, cumaryl, decahydroquinolyl, dithiazolyl, dibenzofuranyl, dibenzothiophenyl, furazanyl, furyl, imidazolyl, imidazolidinyl, indazolyl, indolizinyl, indolyl, isobenzofuranyl, isochromanyl, isoindolyl, isothiazolyl, isoquinolyl, isoxazolyl, morpholinyl, naphthyridinyl, octahydroisoquinolyl, oxazolyl, perimidinyl, phenanthridinyl, phenazinyl, phenothiazinyl, phenoxazinyl, phthalazinyl, piperidyl, piperazinyl, purinyl, pteridinyl, pyranyl, pyrazinyl, pyrazolyl, pyrazolidinyl, pyridazinyl, pyridyl, pyrimidinyl, pyrrolyl, pyrrolinyl, pyrrolidinyl, tetrahydrofuryl, tetrahydroquinolyl, tetrazolyl, thiazolyl, thianthrenyl, thienyl, thiomorpholino, thiomorpholinyl, thiopyranyl, triazolyl, quinolyl, quinoxalyl, quinazolinyl, quinazolinyl, 2H-pyrrolyl, 3H-indolyl, 4H-quinolizinyl, The term carbene has its conventional meaning and particularly refers to a neutral carbon atom with a valence of two, and two electrons (lone pair) available for the formation of a bond. The skilled person will understand that a carbene can be a bivalent carbon donor. Examples of carbenes include, but are not limited to, N-heterocyclic carbenes (NHC) wherein the carbene carbon is part of a nitrogen containing heterocycle, such as an imidazole, and mono-amino-carbenes.

The term borenium cation complex has its conventional meaning and particularly refers to cationic organic boron containing complexes, where the boron atom is positively charged. It is also the case that the positive charge can be delocalised with particular complex structures as resonance structures can exist. Thus, although the borenium cation complex can be schematically reproduced with the cationic charge on the boron atom, it is understood that the positive charge can be represented on other moieties within the complex.

The term aluminium cation complex has its conventional meaning and particularly refers to cationic organic aluminium containing complexes, where the aluminium atom is positively charged. It is also the case that the positive charge can be delocalised with particular complex structures as resonance structures can exist. Thus, although the aluminium cation complex can be schematically reproduced with the cationic charge on the aluminium atom, it is understood that the positive charge can be represented on other moieties within the complex.

The term carbene stabilised cation complex has its conventional meaning and particularly refers to aluminium and borenium cations, preferably borenium cations that form a dative or coordinate covalent bond with the two electrons (lone pair) available for the formation of L-type ligand bond (bond formed via electron pair donation) from a carbene species. Without wishing to be bound by theory, it is understood that carbene species are particularly suited to act as L-type ligands in borenium cation complexes due to the overlap of available p-orbitals on each species that can stabilise the boron centre through conjugation, in addition to a strong sigma boron-carbon bond.

The term halogen or halo has its conventional meaning and particularly refers to F, Cl, Br or I. Preferably halogen may be F or Cl. More preferably, halogen may be F.

The term substituted has its conventional meaning. Specifically, when used with reference to a functional group, it relates to one or more, more specifically up to five, even more specifically one, two or three, four or five of the hydrogen atoms from the functional group being replaced independently of each other by the corresponding number of the defined substituents.

The term optionally substituted has its conventional meaning which is that the group in question can be substituted or unsubstituted with a substituent. Optional substituents include, but are not limited to, alkyl, hydrocarbyl, chlorocarbyl, fluorocarbyl, fluoro-hydrocarbyl, chloro-hydrocarbyl, alkyoxy, aryl, halo and cycloalkyl.

The term frustrated Lewis pair has its conventional meaning and particularly refers to a compound or mixture of compounds containing a Lewis acid and a Lewis base which, because of steric hindrance, cannot combine to form a thermodynamically strongly bound adduct, or may not in fact combine to form an adduct. Preferably, the Lewis acid and Lewis base are separate molecules forming the frustrated pair. It must however be appreciated that the term frustrated Lewis pair is not dependent on the formation of a thermodynamically unstable adduct but applies more generally to any combination of Lewis acid and Lewis base that can heterolytically cleave dihydrogen ($H_2$).

It will be appreciated that any suitable Lewis acid known in the art that can be used as a component of a frustrated Lewis pair capable of cleaving hydrogen is encompassed by the present invention.

Particularly suitable Lewis acids are of the structure of Formula I shown below:

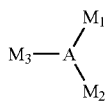

I

Where:
A is a Group 13 element capable of behaving as a Lewis acid, such as B or Al;
$M_1$ and $M_2$ are each independently selected from carbocyclyl, hydrocarbyl or heterocyclyl, each of which is optionally substituted with at least one substituent selected from cyano, halo, hydroxyl, nitro, mesityl, substituted mesityl, $(C_{1-6})$alkyl, $(C_{3-6})$cycloalkyl, $(C_{1-6})$alkoxy, phenyl, $(C_{1-6})$alkylphenyl, heterocyclyl, $(C_{1-6})$alkylheterocyclyl, $SO_2$aryl, $SO_2$alkyl or a linker group which is capable of binding the A atom to a solid support; and
$M_3$ is selected from hydrogen, halo, any one of the groups defined above for $M_1$ or $M_2$.

Preferably, A is selected from boron or aluminium, and even more preferably, A is boron.

Preferably, $M_1$ and $M_2$ are each independently selected from $C_{1-12}$ alkyl, heteroaryl, naphthyl, mesityl, phenyl, each of which is substituted by at least one substituent group selected from cyano, halo, nitro, $(C_{1-6})$alkyl or $(C_{1-6})$alkoxy.

More preferably, $M_1$ and $M_2$ are each independently phenyl or heteroaryl substituted by at least one cyano, halo, nitro, or $(C_{1-6})$ alkoxy groups. Preferably each independently phenyl or heteroaryl is substituted by three to five halo, cyano, or nitro groups.

Preferably, $M_1$ and $M_2$ are each independently phenyl or heteroaryl substituted by an electron withdrawing substituent. Preferably each independently phenyl or heteroaryl is substituted by three to five electron withdrawing substituents.

Even more preferably, $M_1$ and $M_2$ are each independently phenyl or pyrrolyl, each of which is substituted by at least one substituent groups selected from cyano, halo, nitro, $(C_{1-6})$alkyl or $(C_{1-6})$ alkoxy. Preferably, phenyl substituted by cyano, halo, nitro or $(C_{1-6})$alkoxy.

It is highly preferred that $M_1$ and $M_2$ are each independently a mesityl group selected from 2,6-$(CH_3)_2(C_6H_3)$, 3,5-$(CH_3)_2(C_6H_3)$ or 3,5-$(CF_3)_2(C_6H_3)$.

The skilled person will appreciate that $M_1$ and $M_2$ can be identical or different. Preferably $M_1$ and $M_2$ are identical. It will also be understood that $M_3$ may be any one of the groups defined herein for $M_1$ or $M_2$.

Preferably, when $M_1$ and $M_2$ are identical $M_3$ is Hydrogen.

Preferably, $M_1$, $M_2$ and $M_3$ are identical.

When $M_3$ is a linker group, it may be any suitable linker group capable of coupling the central atom (A) of the Lewis acid to a solid support. For example, it may be a functional group capable of reacting with a functional group on the solid support surface to form a covalent bond, or it may be a hydrocarbyl, carbocyclyl, heterocyclyl group which is substituted with a substituent comprising a suitable functional group for coupling the central atom (A) of the Lewis acid to a solid support. The solid could be an organic (polymer-based) or inorganic solid phase. Preferably the solid is a carbon or platinum electrode, even more preferably a carbon electrode.

Preferably, the Lewis acid has the structural Formula II shown below:

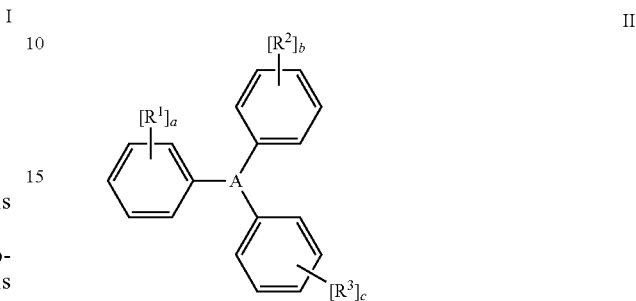

II

Where:
A is as defined above; and
$R^1$, $R^2$ and $R^3$ are each independently selected from amino, cyano, halo, hydroxy, nitro, phenyl, $(C_{1-6})$alkyl, $(C_{3-6})$cycloalkyl, $(C_{1-6})$alkoxy, $(C_{1-6})$alkylphenyl; and each of a, b and c independently represent any integer from zero to five, specifically zero, one, two, three, four or five.

Preferably, $R^1$, $R^2$ and $R^3$ are each electron withdrawing substituents.

Preferably, $R^1$, $R^2$ and $R^3$ are each independently selected from cyano, halo, nitro, $(C_{1-4})$alkyl, $(C_{1-4})$fluoroalkyl, $(C_{1-4})$chloroalkyl, $(C_{1-4})$alkoxy or phenyl.

More preferably, $R^1$, $R^2$ and $R^3$ are each independently selected from cyano, halo, nitro, $(C_{1-4})$alkyl, or $(C_{1-4})$ alkoxy.

Even more preferably, $R^1$, $R^2$ and $R^3$ are each independently selected from cyano, halo, nitro, or $(C_{1-4})$alkoxy.

Preferably, $R^1$, $R^2$ and $R^3$ are each independently selected from chloro, fluoro or cyano. More preferably, $R^1$, $R^2$ and $R^3$ are each independently selected from chloro or fluoro. Even more preferably $R^1$, $R^2$ and $R^3$ each individually represent a mixture of chloro and fluoro substituents according to the formula $Cl_nF_{5-n}$; wherein n represents any integer from zero to five, specifically zero, one, two, three, four or five.

Preferably, $R^1$, $R^2$ and $R^3$ are each independently selected from a $(C_{1-2})$alkylphenyl. Particularly preferred $(C_{1-2})$alkylphenyl groups include 2,6-$(CH_3)_2(C_6H_3)$, 3,5-$(CH_3)_2(C_6H_3)$ or 3,5-$(CF_3)_2(C_6H_3)$.

Each of a, b and c independently represent an integer which is at least one and up to five, specifically one, two, three, four or five. Preferably, each of a, b and c are independently three, four or five. More preferably, each of a, b and c are five.

Preferably, the Lewis acids are stabilised cationic complexes of the structure of Formula Ia shown below:

Ia

Where:
  $A^+$ is a Group 13 ion capable of behaving as a Lewis acid, such as $B^+$ or $Al^+$;
  $M_4$ and $M_5$ are each independently selected from carbocyclyl, hydrocarbyl fluorocarbyl, chlorocarbyl, chlorofluorocarbyl, fluoro-hydrocarbyl, chloro-hydrocarbyl or heterocyclyl, each of which is optionally substituted with at least one substituent selected from cyano, halo, hydroxyl, nitro, mesityl, substituted mesityl, $(C_{1-6})$alkyl, $(C_{3-6})$cycloalkyl, $(C_{1-6})$alkoxy, phenyl, $(C_{1-6})$alkylphenyl, heterocyclyl, $(C_{1-6})$alkylheterocyclyl, $SO_2$aryl, $SO_2$alkyl, or $M_4$ and $M_5$ may be coupled so that they form a four, five, six or seven, eight, nine, or ten atom, saturated or unsaturated, mono- or bicyclic ring, which may optionally comprise one or two additional heteroatoms selected from nitrogen, oxygen or sulphur, and may be optionally substituted with one or more substituent groups selected from amino, cyano, halo, nitro, trifluoromethyl, $(C_{1-6})$alkyl, $(C_{1-6})$alkoxy, or $—S(O)_r—(C_{1-6})$alkyl (where r represents zero, one or two), or a linker group which is capable of binding the $A^+$ ion to a solid support; and
  $M_6$ is an electron pair donor ligand coordinated to $A^+$.

Preferably, $A^+$ is a boron or aluminium cation. More preferably, $A^+$ is a boron cation.

Preferably, $M_4$ and $M_5$ are each independently selected from fluorocarbyl, chlorocarbyl, chloro-fluorocarbyl, fluoro-hydrocarbyl, chloro-hydrocarbyl, $(C_{1-6})$alkyl, aryl, mesitly, or substituted mesityl. Preferably, each of $M_4$ and $M_5$ can independently be $C_6F_6$, $C_6Cl_5$, $2,6-(CH_3)_2(C_6H_3)$, $3,5-(CH_3)_2(C_6H_3)$ or $3,5-(CF_3)_2(C_6H_3)$. Preferably, each of $M_4$ and $M_5$ is independently a mesityl group selected from $2,6-(CH_3)_2(C_6H_3)$, $3,5-(CH_3)_2(C_6H_3)$ or $3,5-(CF_3)_2(C_6H_3)$.

Preferably, $M_4$ and $M_5$ are identical.

Preferably, $M_4$ and $M_5$ are coupled so that they form an eight, nine, or ten atom, saturated mono- or bicyclic ring, preferably 9-BBN.

Preferably, $M_6$ is a strong Lewis base, more preferably a phosphine or a carbene, even more preferably an N-heterocyclic carbene.

Examples of suitable Lewis acids include, but are not limited to, $B(C_6F_5)_3$, $B(C_6Cl_5)_3$, $B(C_6F_5)(C_6Cl_5)_2$, $B(C_6F_5)_2(C_6Cl_5)$, $Al(C_6F_5)_3$, $B(C_6F_4H)_3$, $BCl(C_6F_5)_2$, $[HB(C_6F_5)_2]_n$ where n is 1 or 2, $[(^iPr_2—NHC)(B(2,6-(CH_3)_2C_6H_3)_2)]^+$, $[^iPr_2—NHC)(B(3,5-(CH_3)_2C_6H_3)_2)]^+$ or $[(^iPr_2—NHC)(B(3,5-(CF_3)_2C_6H_3)_2)]^+$. Particularly preferred Lewis acids are $B(C_6F_5)_3$, $B(C_6Cl_5)_3$, $B(C_6F_5)(C_6Cl_5)_2$, $B(C_6F_5)_2(C_6Cl_5)$, $B(C_6Cl_4F)_3$, $[(^iPr_2—NHC)(B(3,5-(CH_3)_2C_6H_3)_2)]^+$ or $[(^iPr_2—NHC)(B(3,5-(CF_3)_2C_6H_3)_2)]^+$.

Any suitable Lewis base that can form a component of a frustrated Lewis pair that can cleave hydrogen is encompassed by the present invention. For example, sterically bulky ethers, alcohols, phosphines or amines such as tri-tert-butyl phosphine. Particularly preferred Lewis bases include, but are not limited to, oxygen containing Lewis base solvents such as water, alcohols, ethers. However, it should be understood that any molecule, complex, ion or fragment that can act as an electron pair donor and react with a Lewis acid to form a Lewis adduct can be considered as a suitable Lewis base. Preferably, the $pK_a$ of the conjugate acid of the Lewis base is about 7, but no less than about −10, in water.

The Lewis base may comprise a secondary or tertiary amine. The secondary or tertiary amine may be an aromatic or an aliphatic amine. Most preferably, no hydrogen is present on the carbon atoms that are covalently bonded to the nitrogen of the amine group. Preferably, the Lewis base may comprise an optionally substituted pyridine compound.

The Lewis base preferably comprises an aromatic substituted pyridine, a non-aromatic amine, a heterocyclic carbene, a phosphorus containing compound, an oxygen containing compound or a sulphur containing compound.

Preferably, the Lewis base is an aromatic substituted pyridine of Formula III shown below:

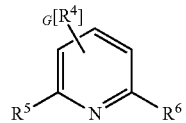

III

Where:
  $R^4$, $R^5$ and $R^6$ are each a substituent group other than hydrogen, or a linker group to connect the compound of Formula III to a solid support. Examples of suitable substituent groups other than hydrogen include, but are not limited to, amino, cyano, halo, nitro, trifluoromethyl, $(C_{1-6})$alkyl, $(C_{1-6})$alkoxy or $—S(O)_r—(C_{1-6})$alkyl (where r represents zero, one or two); and
  G represents any integer from zero to three, specifically zero, one, two or three.

$R^4$ may represent any suitable ring substituent when present. Examples of suitable ring substituents include, but are not limited to, amino, cyano, halo, nitro, trifluoromethyl, $(C_{1-6})$alkyl, $(C_{1-6})$alkoxy, $NH(C_{1-6})$alkyl, $N[(C_{1-6})$alkyl$]_2$, $—S(O)_r—(C_{1-6})$alkyl (where r represents zero, one or two) or aryl. Preferably, G is equal to zero.

Preferably, $R^5$ and $R^6$ are selected from amino, carbocyclyl cyano, halo, heterocyclyl, hydrocarbyl, hydroxyl, $NH(C_{1-6})$alkyl, $N[(C_{1-6})$alkyl$]_2$, $—S(O)_r—(C_{1-6})$alkyl (where r represents zero, one or two). Preferably the hydrocarbly is a $(C_{1-6})$alkyl, such as methyl, ethyl, or t-butyl. Preferably the carbocyclyl is phenyl.

More preferably, $R^5$ and $R^6$ are selected from $(C_{1-6})$alkyl or phenyl. Even more preferably, $R^5$ and $R^6$ are selected from methyl, t-butyl or phenyl.

Preferably, the Lewis base is 2,6-dimethylpyridine or 2,6-di-tert-butylpyridine.

Preferably, the Lewis base is a non-aromatic amine, particularly an aliphatic amine of the general Formula IV shown below:

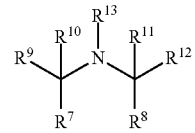

IV

Where:
  $R^7$ and $R^9$ are each independently a $(C_{1-6})$alkyl which may be optionally substituted with any suitable substituent. Examples of suitable substituents include, but are not limited to, amino, cyano, halo, nitro, trifluoromethyl, $(C_{1-6})$alkyl, $(C_{1-6})$alkoxy or $—S(O)_r—(C_{1-6})$alkyl (where r represents zero, one or two).
  or $R^7$ and $R^9$ may be coupled so that, together with the $—C(R^9R^{10})—N(R^{13})—C(R^{11}R^{12})—$ group to which they are attached, they form a five, six or seven atom heterocyclic ring, which may optionally comprise one or two additional heteroatoms selected from nitrogen, oxygen or sulphur, and may be optionally substituted with one or more substituent groups selected from amino, cyano, halo, nitro, trifluoromethyl, $(C_{1-6})$alkyl, $(C_{1-6})$alkoxy, or —S(O)$_r$—$(C_{1-6})$alkyl (where r represents zero, one or two).

$R^9$, $R^{10}$, $R^{11}$ and $R^{12}$ are each a substituent group other than hydrogen, or one $R^9$, $R^{10}$, $R^{11}$ or $R^{12}$ is a linker that links the Lewis base to a solid support; and $R^{13}$ is hydrogen or a linker that links the Lewis base to a solid support.

Preferably, $R^9$, $R^{10}$, $R^{11}$ and $R^{12}$ are all hydrocarbyl, preferably $(C_{1-6})$alkyl. Preferably, $R^9$, $R^{10}$, $R^{11}$ and $R^{12}$ are all methyl.

It will be understood that, $R^7$ and $R^9$ may be taken together with the —C($R^9R^{10}$)—N($R^{13}$)—C($R^{11}R^{12}$)— group to which they are attached, to form a five or six membered heterocyclic ring, which optionally comprises one additional heteroatom selected from nitrogen, oxygen or sulphur. Preferably, $R^7$ and $R^9$ are linked so that, together with the —C($R^9R^{10}$)—N($R^{13}$)—C($R^{11}R^{12}$)— group to which they are attached, they form a piperidine ring.

Preferably, $R^{13}$ is hydrogen.

A preferred Lewis base of the general Formula IV is 2,2,6,6-tetramethylpiperidine.

Preferably, the Lewis base is a heterocyclic carbene of the general Formula V:

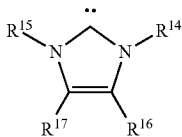

V

Where:
$R^{14}$ and $R^{15}$ are selected from hydrogen or $(C_{1-6})$alkyl;
$R^{16}$ and $R^{17}$ are both selected from amino, cyano, halo, hydrogen, nitro, trifluoromethyl, $(C_{1-6})$alkyl, $(C_{1-6})$alkoxy, NH$(C_{1-6})$alkyl, N[$(C_{1-6})$alkyl]$_2$, —S(O)$_r$—$(C_{1-6})$alkyl (where r represents zero, one or two) or aryl; or any one of $R^{14}$, $R^{15}$, $R^{16}$ and $R^{17}$ is a linker that links the Lewis base to a solid support.

Preferably, $R^{14}$ and $R^{15}$ are each a $(C_{1-6})$alkyl. More preferably, $R^{14}$ and $R^{15}$ are each methyl, ethyl, n-propyl, isopropyl, n-butyl, sec-butyl or tert-butyl.

Preferably, $R^{16}$ and $R^{17}$ are both hydrogen.

Preferably, the Lewis base is a phosphorus containing compound of the general Formula VI

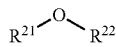

VI

Where:
$R^{18}$, $R^{19}$ and $R^{20}$ are each independently selected from a hydrocarbyl, carbocyclyl, heterocyclyl, each of which is optionally substituted with amino, aryl, cyano, halo, heterocyclyl, nitro, $(C_{1-6})$alkyl or $(C_{1-6})$alkoxy;
or one of $R^{18}$, $R^{19}$ and $R^{20}$ is a linker group that comprises a functional group capable of linking the phosphorus atom to a solid support.

Preferably, $R^{18}$, $R^{19}$ and $R^{20}$ are each independently selected from $(C_{1-6})$alkyl or phenyl, each of which is optionally substituted with amino, cyano, halo, nitro, $(C_{1-6})$alkyl or $(C_{1-6})$alkoxy.

Preferably, $R^{18}$, $R^{19}$ and $R^{20}$ are each independently selected from $(C_{1-6})$alkyl, (e.g. ethyl, t-butyl) or phenyl, each of which is optionally substituted with halo, $(C_{1-6})$alkyl or $(C_{1-6})$alkoxy.

Preferably, $R^{18}$, $R^{19}$ and $R^{20}$ are each independently selected from $(C_{1-6})$alkyl, or phenyl, each of which is optionally substituted with halo, $(C_{1-6})$alkyl or $(C_{1-6})$alkoxy or —(C$_6$F$_5$)$_2$.

Preferably, $R^{19}$ and $R^{20}$ are each phenyl substituted with one, two or three methyl groups and $R^{18}$, is ethyl, t-butyl or phenyl substituted with halo or B(C$_6$F$_5$)$_2$.

Preferably, $R^{18}$, $R^{19}$ and $R^{20}$ are each independently selected from t-butyl or phenyl substituted with one, two or three methyl groups.

Preferably, the Lewis base is an oxygen containing compound of the general Formula VII.

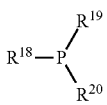

VII

Where:
$R^{21}$ and $R^{22}$ are each independently selected from hydrogen, hydrocarbyl, carbocyclyl, heterocyclyl, each of which is optionally substituted with amino, aryl, cyano, halo, heterocyclyl, nitro, $(C_{1-6})$alkyl or $(C_{1-6})$alkoxy;
or $R^{21}$ and $R^{22}$ may be coupled so that they form a four, five, six or seven atom, saturated or unsaturated ring, which may optionally comprise one or two additional heteroatoms selected from nitrogen, oxygen or sulphur, and may be optionally substituted with one or more substituent groups selected from amino, cyano, halo, nitro, trifluoromethyl, $(C_{1-6})$alkyl, $(C_{1-6})$alkoxy, or —S(O)$_r$—$(C_{1-6})$alkyl (where r represents zero, one or two).

Preferably, $R^{21}$ and $R^{22}$ are each independently selected from hydrogen, amino, aryl, cyano, halo, heterocyclyl, nitro, $(C_{1-6})$alkyl or $(C_{1-6})$alkoxy, preferably $(C_{1-6})$alkyl.

Preferably, $R^{21}$ and $R^{22}$ are coupled so that they form a five, six or seven atom, saturated or unsaturated ring, which may optionally comprise one or two additional heteroatoms selected from nitrogen, oxygen or sulphur, and may be optionally substituted with one or more substituent groups selected from halo, trifluoromethyl, $(C_{1-6})$alkyl or $(C_{1-6})$alkoxy, for example N-methylmorpholine and dioxanes. More preferably, $R^{21}$ and $R^{22}$ are linked so that they are attached to form a furan, preferably tetrahydrofuran (THF).

Preferably, $R^{21}$ and $R^{22}$ are identical, preferably selected from hydrogen or $(C_{1-6})$alkyl. More preferably, $R^{21}$ and $R^{22}$ are hydrogen (i.e. water).

Preferably, $R^{21}$ and $R^{22}$ represent the same moiety forming an ester, carbonyl or carboxyl group, wherein $R^{21}$/$R^{22}$ is selected from hydrocarbyl, carbocyclyl, heterocyclyl, which is optionally substituted with amino, aryl, cyano, halo, heterocyclyl, nitro, $(C_{1-6})$alkyl or $(C_{1-6})$alkoxy, for example dimethylacetamide, diethylacetamide, acetamide.

Preferably, the Lewis base is a sulphur containing compound of the general Formula VIII.

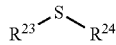

VIII

Where:

$R^{23}$ and $R^{24}$ are each independently selected from hydrogen, hydrocarbyl, carbocyclyl, heterocyclyl, each of which is optionally substituted with amino, aryl, cyano, halo, heterocyclyl, nitro, $(C_{1-6})$alkyl or $(C_{1-6})$alkoxy;

or $R^{23}$ and $R^{24}$ may be coupled so that they form a four, five, six or seven atom, saturated or unsaturated ring, which may optionally comprise one or two additional heteroatoms selected from nitrogen, oxygen or sulphur, and may be optionally substituted with one or more substituent groups selected from amino, cyano, halo, nitro, trifluoromethyl, $(C_{1-6})$alkyl, $(C_{1-6})$alkoxy, or $—S(O)_r—(C_{1-6})$alkyl (where r represents zero, one or two).

Preferably, $R^{23}$ and $R^{24}$ are each independently selected from hydrogen, amino, aryl, cyano, halo, heterocyclyl, nitro, $(C_{1-6})$alkyl or $(C_{1-6})$alkoxy, preferably $(C_{1-6})$alkyl.

More preferably, $R^{23}$ and $R^{24}$ are coupled so that they form a five, six or seven atom, saturated or unsaturated ring, which may optionally comprise one or two additional heteroatoms selected from nitrogen, oxygen or sulphur, and may be optionally substituted with one or more substituent groups selected from halo, trifluoromethyl, $(C_{1-6})$alkyl or $(C_{1-6})$alkoxy. Even more preferably, $R^{23}$ and $R^{24}$ are linked so that they are attached to form a five membered saturated or unsaturated thiophene ring. Most preferably, $R^{23}$ and $R^{24}$ form a five membered saturated thiophene ring, such as tetrahydrothiophene.

Preferably, $R^{23}$ and $R^{24}$ are identical, preferably selected from hydrogen or $(C_{1-6})$alkyl. Even more preferably, $R^{23}$ and $R^{24}$ are hydrogen.

Preferably, $R^{23}$ and $R^{24}$ represent the same moiety forming a thio-ester, thio-carbonyl or thio-carboxyl group, wherein $R^{23}/R^{24}$ is selected from hydrocarbyl, carbocyclyl, heterocyclyl, which is optionally substituted with amino, aryl, cyano, halo, heterocyclyl, nitro, $(C_{1-6})$alkyl or $(C_{1-6})$alkoxy.

In addition to the above sulphur containing compounds, the Lewis base may also be an optionally substituted sulfolane or an optionally substituted dialkyl sulfoxide.

The term solvent has its conventional meaning and particularly refers to a liquid or mixture of liquids that can be used in fuel cell applications, specifically to dissolve another substance to form a solution. Typical fuel cell solvents include, but are not limited to phenyls and aryls such as toluene, benzene, chlorocarbyls, fluorocarbyls, hydrofluorocarbyls and hydrochlorocarbyls such as dichloromethane, 1,2-dichloroethane, tetrachloroethane, and halogenated phenyls and aryls such as fluorobenzene, chlorobenzene, and bromobenzene.

In addition, the skilled person will appreciate that solvents can also exhibit Lewis acidic or Lewis basic properties. Therefore solvents can be described as Lewis acid solvents and Lewis base solvents. In this connection, the term Lewis base solvent encompasses compounds of Formulas III, IV, V, VI, VII and VIII, and any permutations described previously. Specifically, the term Lewis base solvent refers to nitrogen compounds such as N-methylmorpholine, nitriles, imidazole; phosphorous compounds such as phosphines; oxygen containing compounds such as water, ethers (symmetric and non-symmetric dialkyl and diary) ethers), dioxane, furans (THF), carbonyls (acetone and methylethylketone), amides (dimethylacetamide, diethylacetamide, acetamide) alcohols (mono, bi, tri or tert alcohols of alkyls, aryls and phenyls); sulphur containing compounds such as thiophene, tetrahydrothiophene, dimethylsulfoxide and sulfolane. Preferably, Lewis base solvent refers to THF or water.

In addition, the skilled person will appreciate that the present invention may also comprise a battery solvent or combinations of one or more battery solvents. Typically battery solvents include, but are not limited to, allylmethylsulfone, diethylcarbonate, diethylsulfite, dimethylcarbonate, ethylene sulphite, ehtylmethyl carbonate, fluoroethyolenecarbonate, propylene sulphate, polyethyleneoxide and polyethyleneglycol.

It will be understood that the term solvent also encompasses mixtures and combinations of any of the above mentioned compounds.

The expression fuel cell is used to describe a fuel cell that can be a one directional fuel cell (i.e. configured to deliver energy) or can be a reversible fuel cell, such as a rechargeable fuel cell, which is capable of operating in both power delivery and energy storage mode (i.e. configured to store and deliver energy). Thus, it will be appreciated that the expression fuel cell describes a device which generates energy or dissipates stored energy, operating in a power delivery mode, and also as an energy storage device, operating as a battery or capacitor.

In accordance with standard terminology in the field of fuel cells, the terms anode and cathode are defined by the functions of the electrodes in the power delivery mode. To avoid confusion, the same terms are maintained to denote the same electrodes throughout the various modes of operation of the fuel cell, for example, recharge, capacitor or power storage.

It will be understood that any electrochemical reactions described as being at an electrode (anode or cathode) can occur anywhere around, on or about the electrode.

DETAILED DESCRIPTION

The fuel cell according to the first aspect of the invention is able to act as an energy generating device, operating in a power delivery mode, and also as an energy storage device, operating as a battery or capacitor.

During operation as an energy generating device such as a fuel cell, an electrochemically active species is oxidised at the anode and an electrochemically active species is reduced at the cathode. The electrochemically active species reacting at the anode is the Lewis acid hydride formed via the heterolytic cleavage of dihydrogen ($H_2$). The overall redox reaction at the anode is:

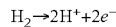
$$H_2 \rightarrow 2H^+ + 2e^-$$

which is effected by the following FLP electrocatalysed process:

$$LA + H_2 + LB \Leftrightarrow LAH^- + LBH^+$$

$$LAH^- \rightarrow LA + H^+ + 2e^-$$

Where LA=Lewis acid, and LB=Lewis base

Preferably, the reaction occurs in solution, the solution preferably further comprising a solvent and/or an electrolyte of the type defined above.

During operation as an energy storage device, such as a battery or capacitor, an amount of Lewis acid and Lewis base components in the electrolyte may be spatially separated. In this mode, preferably an amount of Lewis acid and Lewis base is immobilised onto the anode and cathode, respectively, preferably with an amount of free Lewis acid and base in the electrolyte. The Lewis acid immobilised onto one electrode reacts with hydrogen to form the Lewis acid hydride, and the electrode subsequently becomes negatively charged, whilst the Lewis base is attached to another electrode and becomes protonated and positively charged. This separation of charges stores the chemical energy of hydrogen as electrical potential energy or voltage.

As the energy storage device is discharged the Lewis acid hydride is oxidised and the protonated Lewis base is reduced to form hydrogen.

Preferably, the heterolytic cleavage of dihydrogen ($H_2$) is generated by the use of a frustrated Lewis pair. On exposure to dihydrogen, frustrated Lewis pairs can heterolytically cleave dihydrogen to form a Lewis acid hydride and a protonated Lewis base. Reaction Scheme (I) demonstrates the heterolytic cleaving of hydrogen ($H_2$) to produce a Lewis acid/base complex. The complex can be further subjected to an electrochemical redox reaction.

Scheme (I)

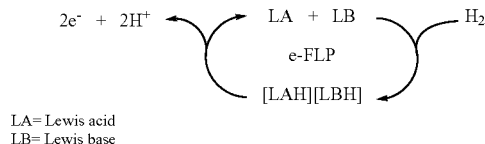

LA = Lewis acid
LB = Lewis base

In Scheme (I), dihydrogen ($H_2$) is introduced to the electrocatalytic frustrated Lewis pair system (e-FLP). The frustrated Lewis pair heterolytically cleaves the dihydrogen to create a salt. The Lewis acid hydride component of the salt is then electrochemically oxidised to form two protons and two electrons.

It has been found that the kinetics of dihydrogen cleavage via the combination of a Lewis acid with a Lewis base is the rate-determining step in the overall electrochemical oxidation of hydrogen shown in Scheme (I). Furthermore, it is understood that the choice of Lewis base component may also affect the rate of hydrogen cleavage. However, it is difficult to select and/or tune an appropriate Lewis base because some Lewis bases can also affect the redox chemistry of the system.

It has been surprisingly found that combining a Lewis acid with an oxygen containing Lewis base solvent results in improved reaction kinetics compared to other Lewis acid and base combinations. Oxygen containing Lewis base solvents include, but are not limited to, water, alcohols, ethers, furans, cycloalkyl ethers and cycloalkyl alcohols. In particular, water, alcohols, ethers and cycloalkyl ethers are preferred. Without wishing to be bound by theory, it is understood that the improved reaction kinetics arise from the rapid reversibility of the proton transfer between oxygenated species (e.g. $H_2O$, ethers, alcohols etc.), thereby increasing proton solvation and mobility through the medium in comparison with more conventional nitrogen or phosphorous-centred Lewis bases. In addition, the high effective concentration of the Lewis base, when present as solvent, relative to Lewis acid, also increases the concentration of intermolecular Acid:$H_2$:Base interactions, which precede dihydrogen cleavage.

Furthermore, it has been found that the oxygen containing solvent tetrahydrofuran (THF) can be used with a Lewis acid in the absence of an additional Lewis base to undergo in situ electrocatalysed hydrogen oxidation via a frustrated Lewis pair system with improved reaction kinetics.

Frustrated Lewis pair systems have been previously used as ring-opening catalysts for cyclical molecules such as THF (Birkmann et al; *Organometallics;* 2010, 29, 5310-5319 and Aouissi et al; *Molecules;* 2010, 15, 1398-1407). It is therefore unexpected that THF is stable as a Lewis base in a frustrated Lewis pair system and also that THF can be used as a Lewis base with a Lewis acid to activate and heterolytically cleave hydrogen. It is also unexpected that the reaction kinetics of the electrocatalysed frustrated Lewis pair system is improved compared with systems comprising a Lewis acid with a Lewis base.

An additional benefit to using THF is that THF can act as a protecting system for Lewis acids which are not water tolerant. The $pK_a$ of the protonated THF in the electrocatalysed frustrated Lewis pair system is similar to the $pK_a$ of THF in water. The protonated THF species formed during heterolytic dihydrogen cleavage act to prevent the formation of any aqua-adducts of the Lewis acids.

It has also been found that the radical anion intermediate of the oxidised Lewis acid hydride can undergo side reactions with the solvent. These reactions are shown in Scheme (II) with $B(C_6F_5)_3$ as the Lewis acid. However, the specific compounds are provided for reference only, and it is anticipated that all Lewis acid hydrides formed from the heterolytic cleaving of dihydrogen via a frustrated Lewis pair would follow a similar reaction scheme.

Scheme (II)

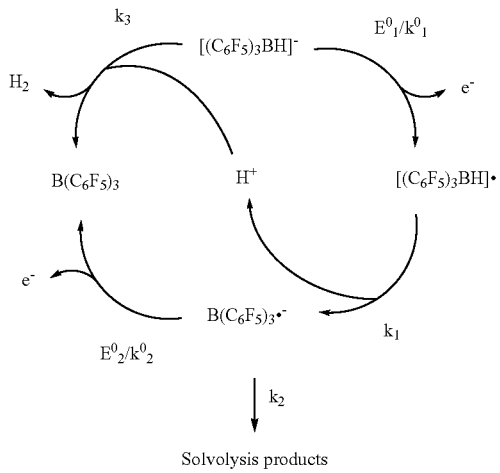

Solvolysis products

The mechanism in Scheme (II) shows two reaction pathways for the Lewis acid borohydride. Hydrogen has been heterolytically cleaved by the frustrated Lewis pair to form the Lewis acid borohydride shown at the top of the mechanism. Without wishing to be bound by theory, it is understood that there are two discrete reaction pathways available for the hydride. The first pathway (shown anticlockwise as $K_3$) is the reverse of the heterolytic hydrogen cleavage, thereby producing the aromatically substituted borane from the borohydride in the presence of free protons. This pathway is undesired as it reduces the electrocatalytic activity of the frustrated Lewis pair.

The desired reaction (shown clockwise as $E^o_1/k^o_1 \rightarrow K_1 \rightarrow E^o_2/K^o_2$) is the oxidation of the borohydride to liberate electrons and hydrogen. However, the anion radical intermediate formed via this pathway is subject to solvolytic side reactions ($k_2$) that leads to a reduction in available active catalyst and also catalytic inefficiency. Therefore the solvolytic side reactions of any radical anion intermediates should be avoided.

It has been discovered that these solvolytic side reactions can be prevented by steric protection of the central boron atom. For example, perchlorinated aryl boranes, such as $B(C_6Cl_5)_3$, $(C_6F_5)B(C_6Cl_5)_2$ and $(C_6F_5)_2B(C_6Cl_5)$, provide enough steric shielding to the central boron atom such that they undergo a reversible one electron reduction with no observed solvolytic side reactions.

It has also been found that these solvolytic side reactions can also be prevented by electronic stabilisation of the radical anion intermediate using a strong base to stabilise a borenium cation Lewis acid derivative, specifically, using carbene species to stabilise borenium cation Lewis acid derivatives, preferably N-heterocyclic carbene (NHC) stabilised borenium cation Lewis acid derivatives. In addition, the use of carbene stabilised borenium cation Lewis acid derivatives in the oxidation of hydrogen has shown a significant reduction of the oxidation overpotential required. The preferred N-heterocyclic carbene (NHC) stabilised borenium cation Lewis acid derivatives are compounds of the general Formula IX below:

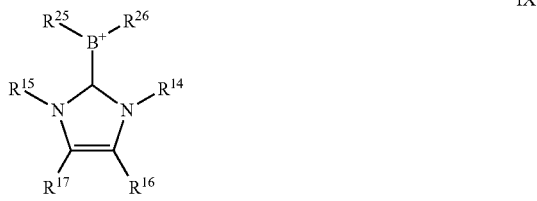

IX where $R^{14}$, $R^{15}$, $R^{16}$ and $R^{17}$ have the same meaning as above; and $R^{25}$ and $R^{26}$ are each independently selected from carbocyclyl, hydrocarbyl, fluorocarbyl, chlorocarbyl, chlorofluorocarbyl, fluoro-hydrocarbyl, chloro-hydrocarbyl or heterocyclyl, each of which is optionally substituted with at least one substituent selected from cyano, halo, hydroxyl, nitro, mesityl, substituted mesityl, $(C_{1-6})$ alkyl, $(C_{3-6})$cycloalkyl, $(C_{1-6})$alkoxy, phenyl, $(C_{1-6})$ alkylphenyl, heterocyclyl, $(C_{1-6})$alkylheterocyclyl.

Preferably, $R^{14}$ and $R^{15}$ are each a $(C_{1-6})$alkyl. More particularly, $R^{14}$ and $R^{15}$ are each independently selected from methyl, ethyl, n-propyl, isopropyl, n-butyl, sec-butyl or tert-butyl.

Preferably, $R^{16}$ and $R^{17}$ are independently either halo or hydrogen. More preferably, $R^{16}$ and $R^{17}$ are halo, preferably fluoro or chloro, even more preferably fluoro.

Preferably, $R^{25}$ and $R^{26}$ represent a 9 borabicyclo[3.3.1] nonane bridge or each of $R^{25}$ and $R^{26}$ can independently be a $C_6F_5$, $C_6Cl_5$, 2,6-$(CH_3)_2(C_6H_3)$, 3,5-$(CH_3)_2(C_6H_3)$ or 3,5-$(CF_3)_2(C_6H_3)$. More preferably, each $R^{25}$ and $R^{26}$ are a mesityl group selected from 2,6-$(CH_3)_2(C_6H_3)$, 3,5-$(CH_3)_2(C_6H_3)$ or 3,5-$(CF_3)_2(C_6H_3)$.

Preferably, $R^{25}$ and $R^{26}$ are identical.

Typically, conventional fuel cells comprise an electrolyte which is invariably aqueous. In contrast, the electrolyte in the hydrogen fuel cell of the present invention may comprise an aqueous electrolyte, or a non-aqueous electrolyte, or a mixed aqueous:non-aqueous electrolyte system in any v:v ratio. Preferably the electrolyte solution is itself Lewis basic. More preferably the electrolyte is a THF solution.

When the fuel cell is configured to store energy, the electrolyte is preferably non-aqueous, more preferably ether solvents. Most preferably, THF is the electrolyte solvent.

The fuel cell may further comprise a proton-permeable permeable selective membrane separating the anode side of the fuel cell from the oxygen-reduction reaction occurring at the cathode. In effect this creates an anode compartment and a cathode compartment of the fuel cell. Preferred membranes are those made of perfluorinated ionomers, such as Nafion. Preferably the membrane is absent.

The material of the electrode(s) in either the energy generation configuration (fuel cell) or the energy storage configuration (battery/capacitor) can be selected from known electrode materials. For example, the electrode can be gold, platinum or any other suitable metal material. In order to reduce costs, graphitic carbon based materials (for example: glassy (vitreous) carbon, graphite, pyrolytic graphite, carbon nanotubes (multiwalled or single-walled) and graphene or graphene oxide) are particularly preferred.

Preferably, the Lewis acid can be immobilised onto the electrode surface. More preferably, the Lewis acid is immobilised onto one electrode surface, and the Lewis base is separately immobilized onto the surface of a second electrode.

When the fuel cell of the present invention is in power delivery mode, oxygen may be reduced at the cathode side of the fuel cell in the presence of freely-solvated protons or protonated Lewis base. Freely-solvated protons or protonated Lewis base may arise from dihydrogen cleavage by the frustrated Lewis pair and/or the oxidation of the Lewis acid hydride at the anode the fuel cell. In this embodiment, the reaction at the cathode is as follows:

$$2H^+ + 2e^- + \tfrac{1}{2}O_2 \rightarrow H_2O.$$

It will be appreciated that the various features described above for the fuel cell of the first aspect may be present in combination mutatis mutandis.

In a second aspect of the invention is provided a method of electrocatalytically oxidising dihydrogen ($H_2$) using a Lewis acid and a Lewis base, comprising a Lewis acid as defined in the first aspect, and a Lewis base as defined in the first aspect. All preferred features of the Lewis acid and Lewis as defined in first aspect of the invention apply equally to the second aspect of the invention mutatis mutandis.

The third aspect of the invention provides an electrode in combination with a Lewis acid hydride formed via the heterolytic cleavage of dihydrogen ($H_2$) using a Lewis acid and a Lewis base, comprising a Lewis acid as defined in the first aspect, and a Lewis base as defined in the first aspect. All preferred features of the first aspect of the invention apply to the third aspect of the invention mutatis mutandis.

BRIEF DESCRIPTION OF THE FIGURES

The present invention will now be described, by way of example, with reference to the accompanying drawings in which.

DETAILED DESCRIPTION OF THE FIGURES

Figure 1:
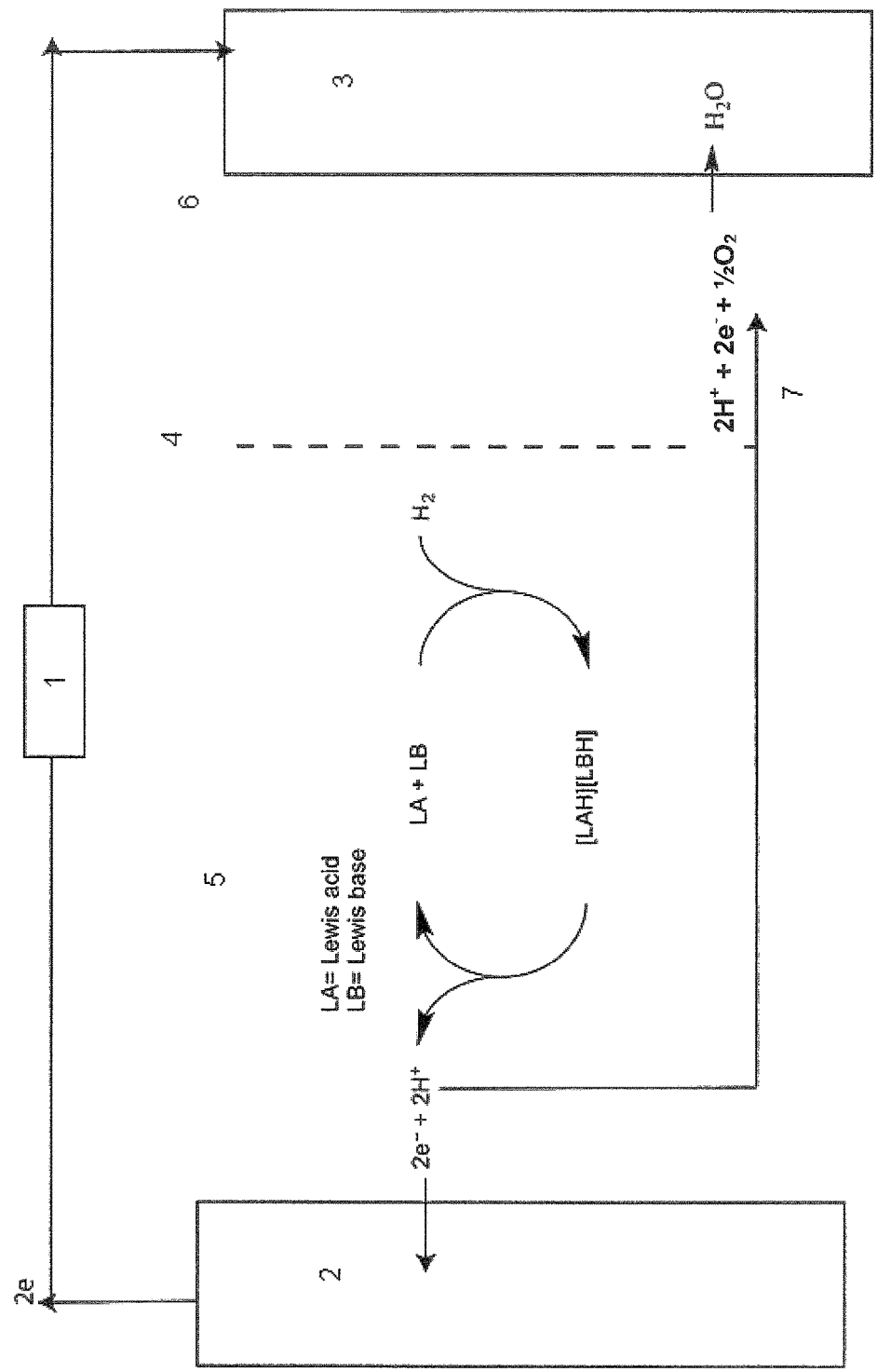
FIGS. 1 and 2 are schematic views of fuel cells of the present invention.

FIG. 1 shows a schematic of a fuel cell with a load (1). The first electrode is the anode (2) and the second electrode is the cathode (3). The electrochemically active species, [LAH]$^-$, is supplied to the anode and is dissolved in liquid THF solution electrolyte.

In power delivery mode, the material at the anode (2) is oxidised according to the following half reaction, and releases protons into the electrolyte:

The oxidised proton can pass from through a membrane (4) from the anodic compartment (5) to the cathodic compartment (6). An additional proton is liberate from the Lewis base, wherein the two protons are combined with oxygen and reduced to water according to the half reaction:

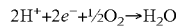

The passage of protons from the anodic compartment to the cathodic compartment balances the charge and completes the electrical circuit.

Figure 2:
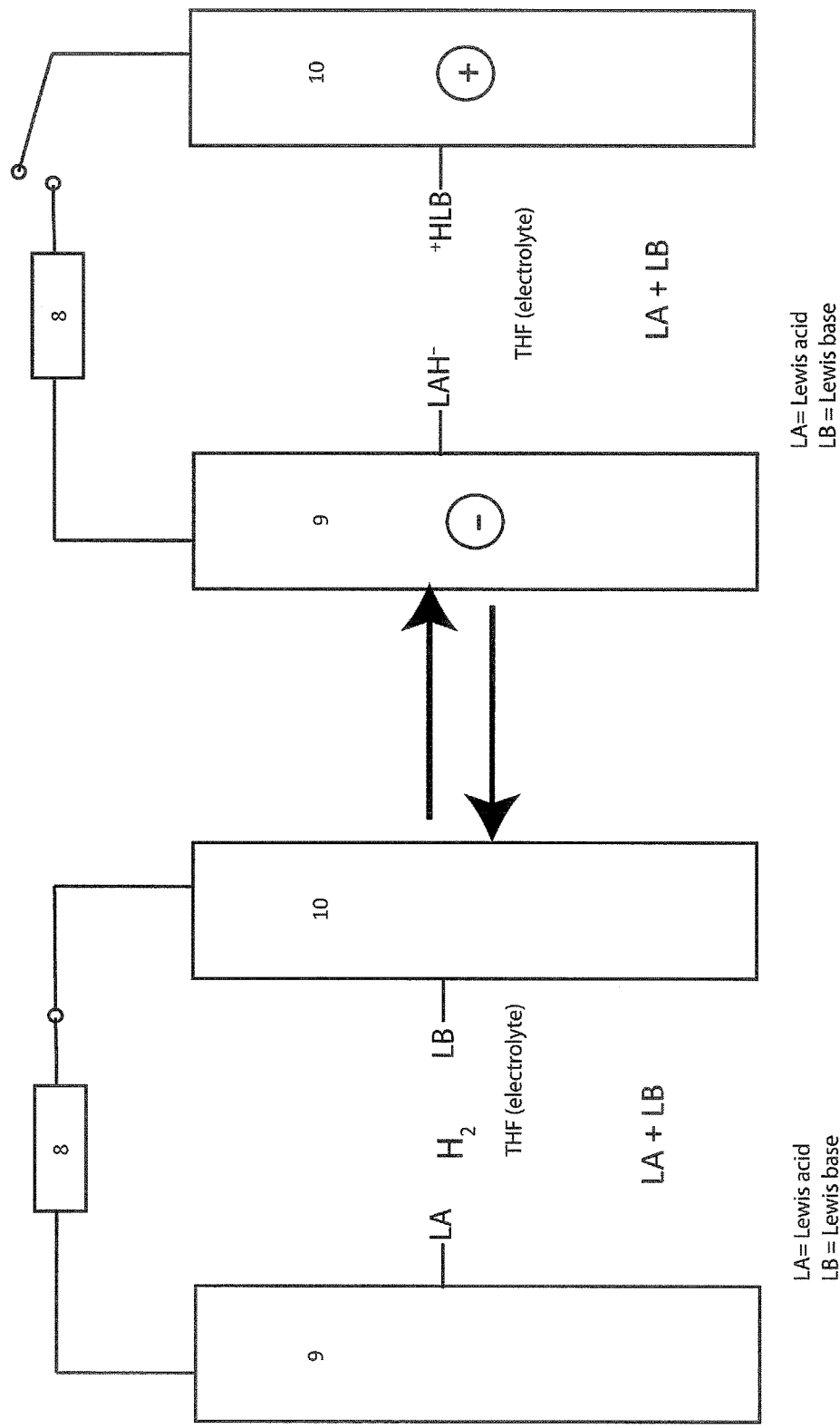

FIG. 2 shows a schematic of a fuel cell in both power delivery mode and power storage mode. A load (8) is applied to the fuel cell on the left hand side of the Figure, causing it to discharge. Lewis acid is immobilised onto the anode (9) and is readily oxidised into the Lewis acid form (LA) following the above reaction scheme. Protonated Lewis base is immobilised on the cathode (10) and is readily deprotonated into the Lewis base (LB).

In power storage mode, a load (8) is not applied and the fuel cell is charged by converting immobilised Lewis acid into the Lewis acid hydride (LBH$^-$) at the anode and also converting immobilised Lewis base into the protonated Lewis base (LBH$^+$) at the cathode. Once a load is applied the fuel cell discharges by liberating protons from oxidation and deprotonating of the immobilised Lewis acid and base, respectively.

Figure 3:
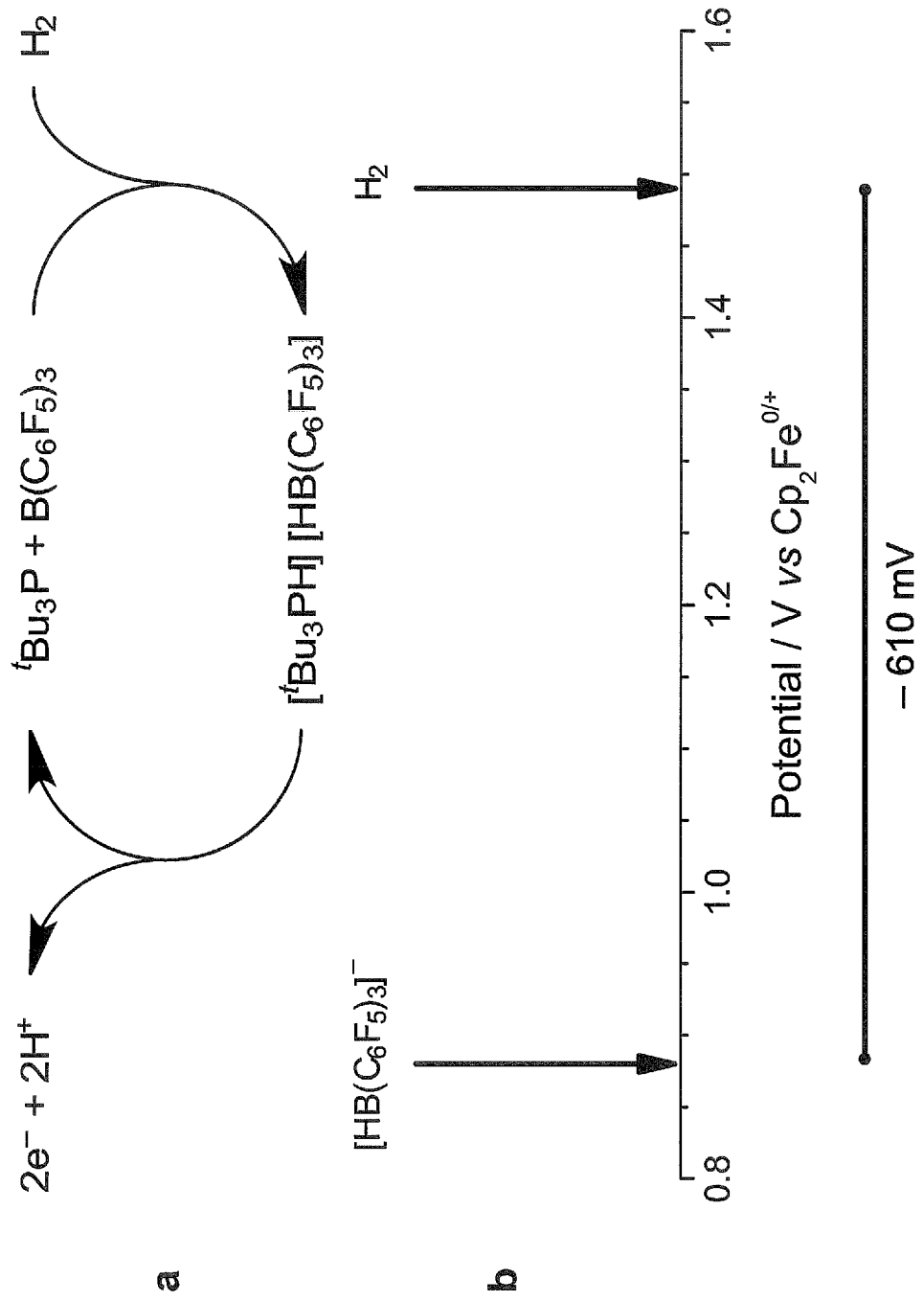
FIG. 3 is a schematic demonstrating the reduced amount of overpotential required to oxidise a specific aromatically substituted borohydride.
Figure 6:
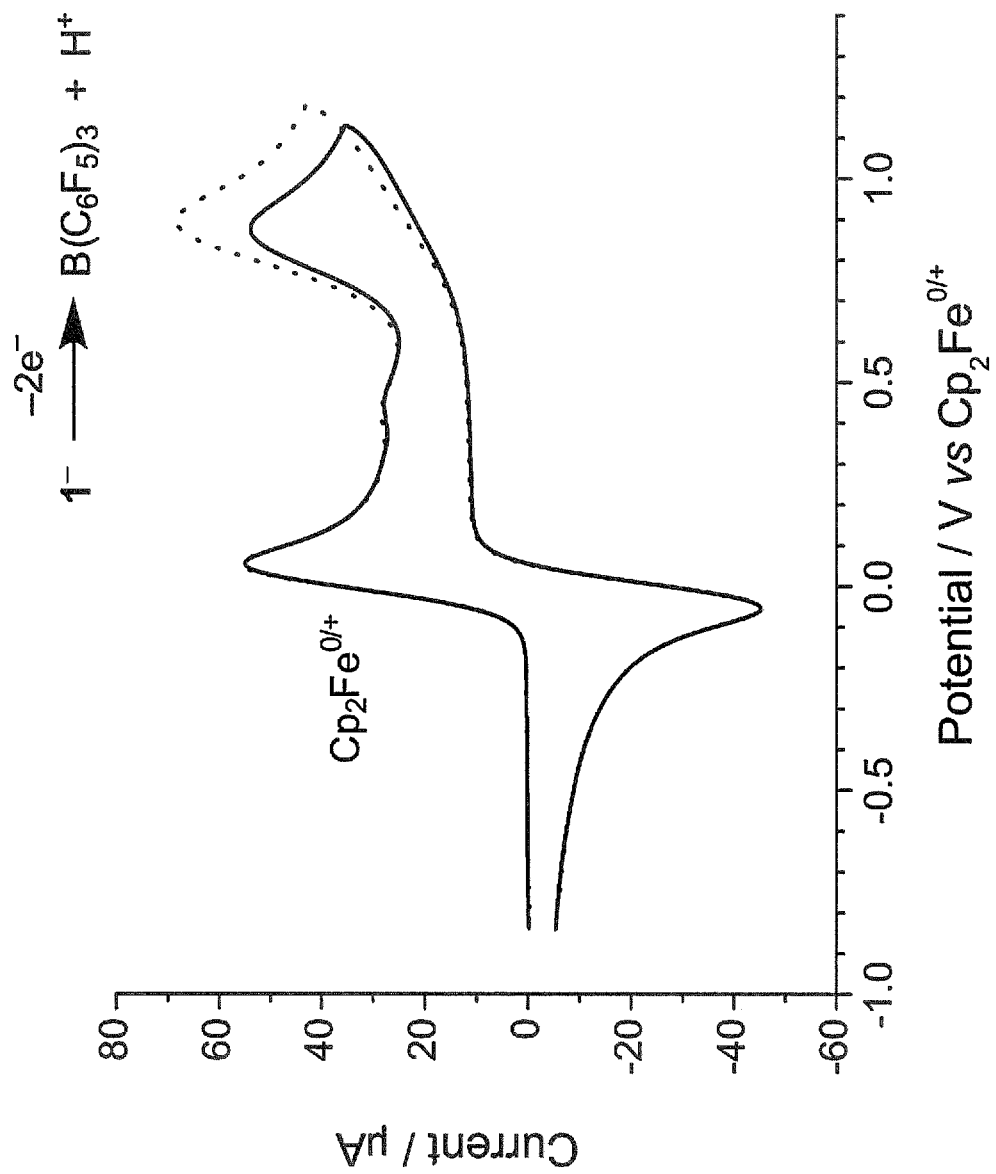
FIG. 6 is a cyclic voltammogram showing the oxidation of a specific aromatically substituted borohydride.
Figure 7:
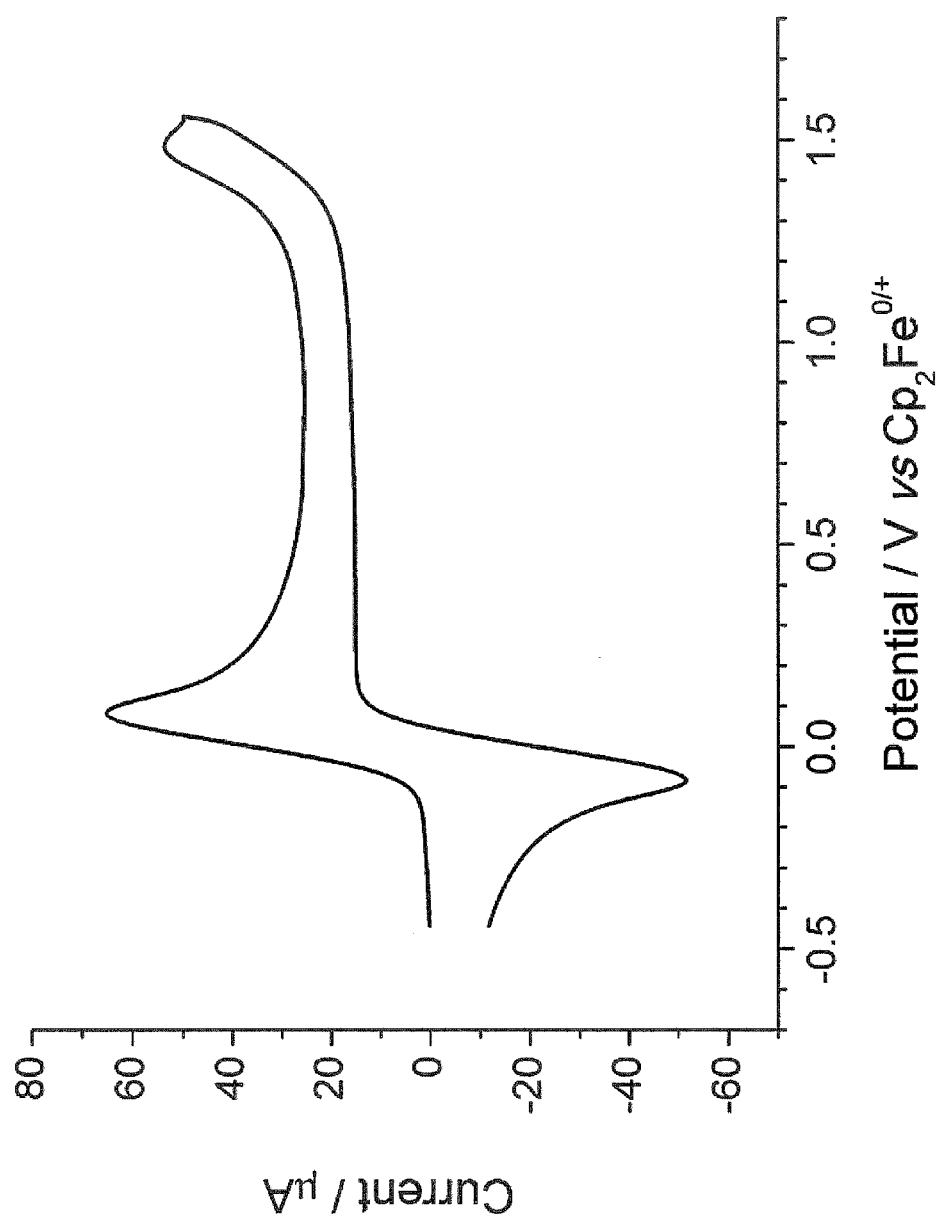
FIG. 7 is a cyclic voltammogram showing the oxidation of dihydrogen on a GCE.
Figure 8:
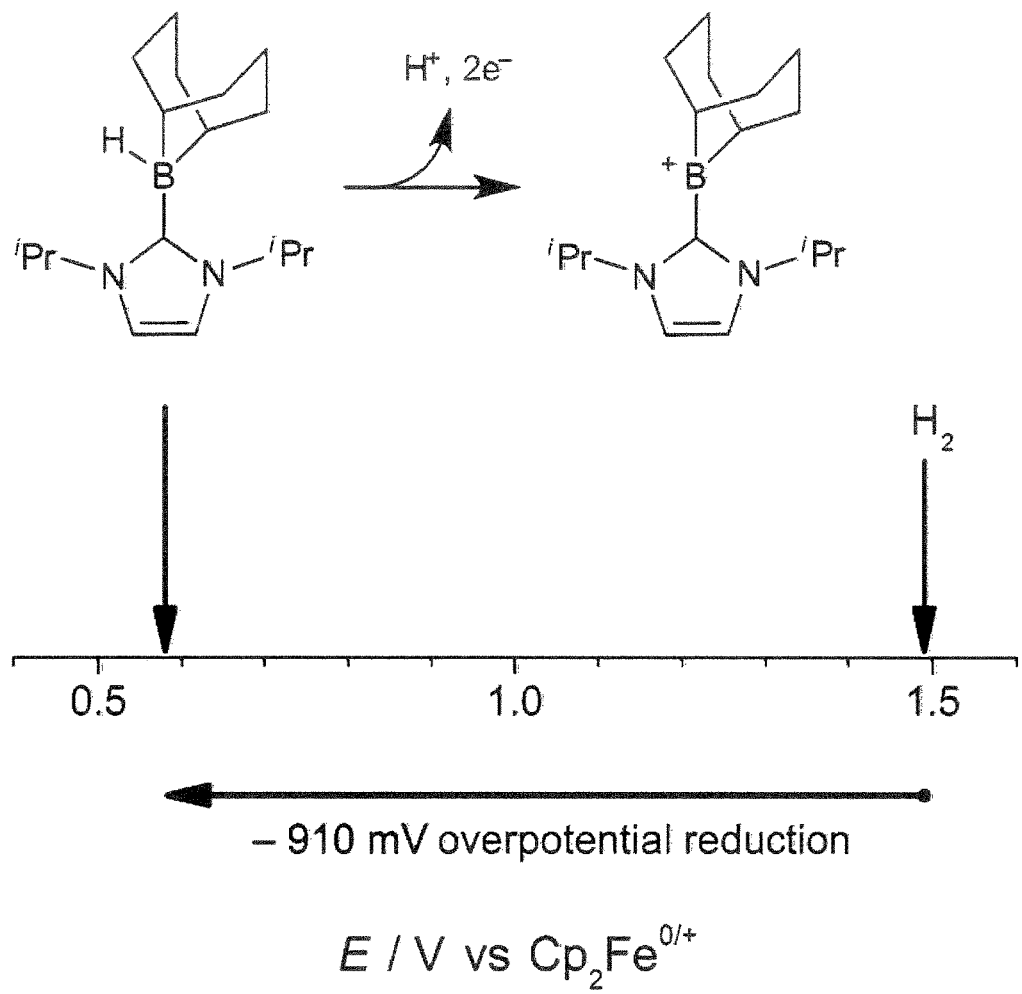
FIG. 8 is a schematic demonstrating the reduced amount of overpotential required to oxidise a specific N-heterocyclic carbene (NHC) stabilised borenium cation Lewis acid, (N,N-($^{i}$Pr)imidazole-2-ylidene)(9-borabicylco[3.3.1]nonane), relative to the oxidation of dihydrogen.

FIGS. 3 to 11 show the experimental results. Specifically, FIGS. 3 and 8 show the decreased overpotential required to oxidise hydrogen using a frustrated Lewis pair, wherein the Lewis acid is B(C$_6$F$_5$)$_3$ and N,N-($^{i}$Pr)imidazole-2-ylidene)(9-borabicylco[3.3.1]nonane, respectively, relative to the oxidation of dihydrogen.

Figure 4:
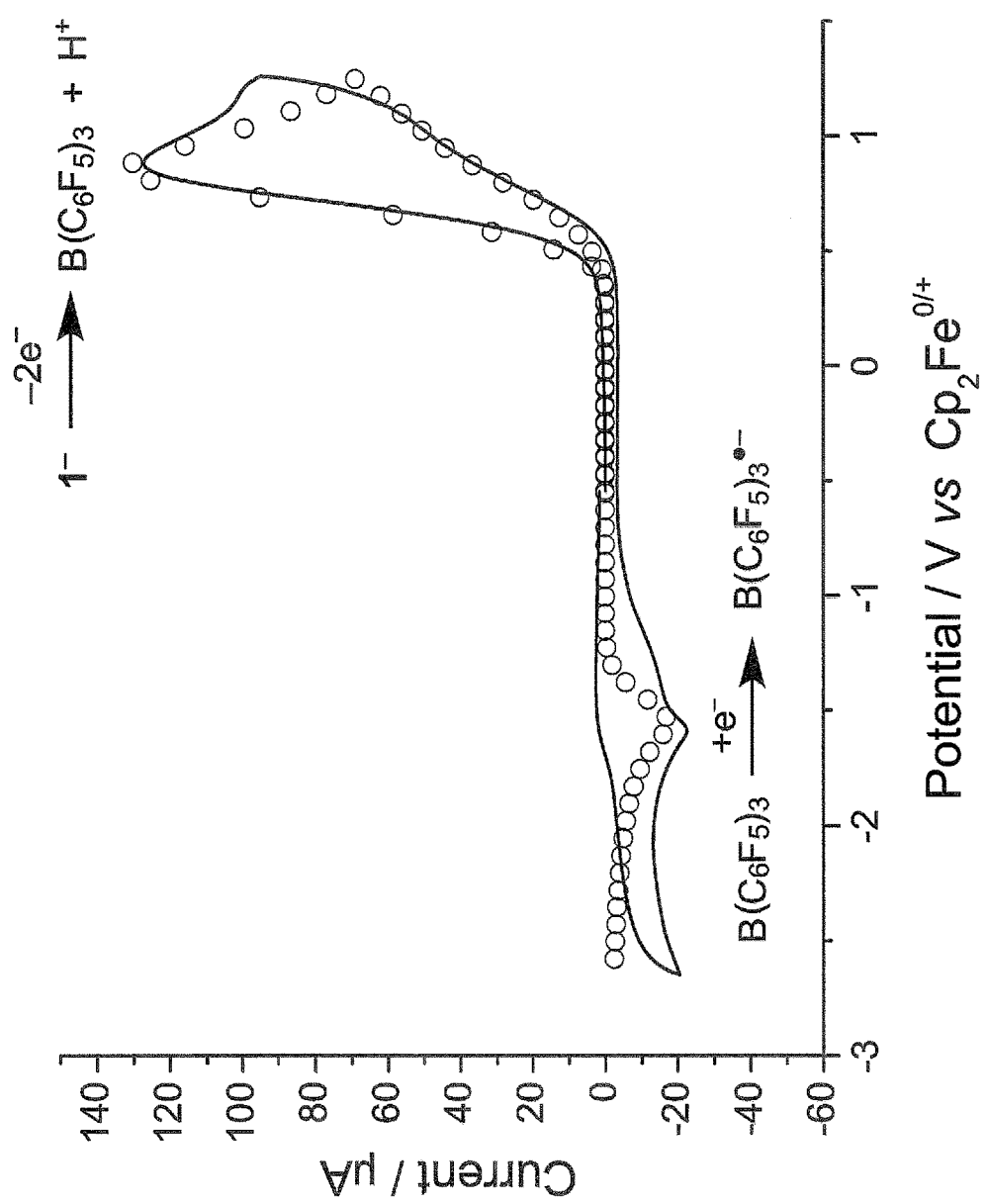
FIG. 4 is a cyclic voltammogram showing the oxidation of a specific aromatically substituted borohydride.

FIG. 4 shows the electrochemical oxidation of the Lewis acid hydride, wherein the Lewis acid is B(C$_6$F$_5$)$_3$, wherein the bold line represents experimental data and the non-solid circles represent best fit data.

Specifically, FIG. 4 shows a Cyclic voltammograms of a 4.9 mM solution of [$^{n}$Bu$_4$N][HB(C$_6$F$_5$)$_3$] in CH$_2$Cl$_2$ recorded at voltage scan rates of 1000 mVs$^{-1}$ over the full scan range on a glassy carbon electrode (GCE). Solid lines are experimental data; open circles are best fit simulated data. The oxidation wave corresponds to the oxidation of [HB(C$_6$F$_5$)$_3$]$^-$ whilst the reduction wave corresponds to reduction of regenerated B(C$_6$F$_5$)$_3$ (as demonstrated in Lawrence, E. J.; Oganesyan, V. S.; Wildgoose, G. G.; Ashley, A. E. *Dalton Trans.* 2013, 42, 782-789.).

Figure 5:
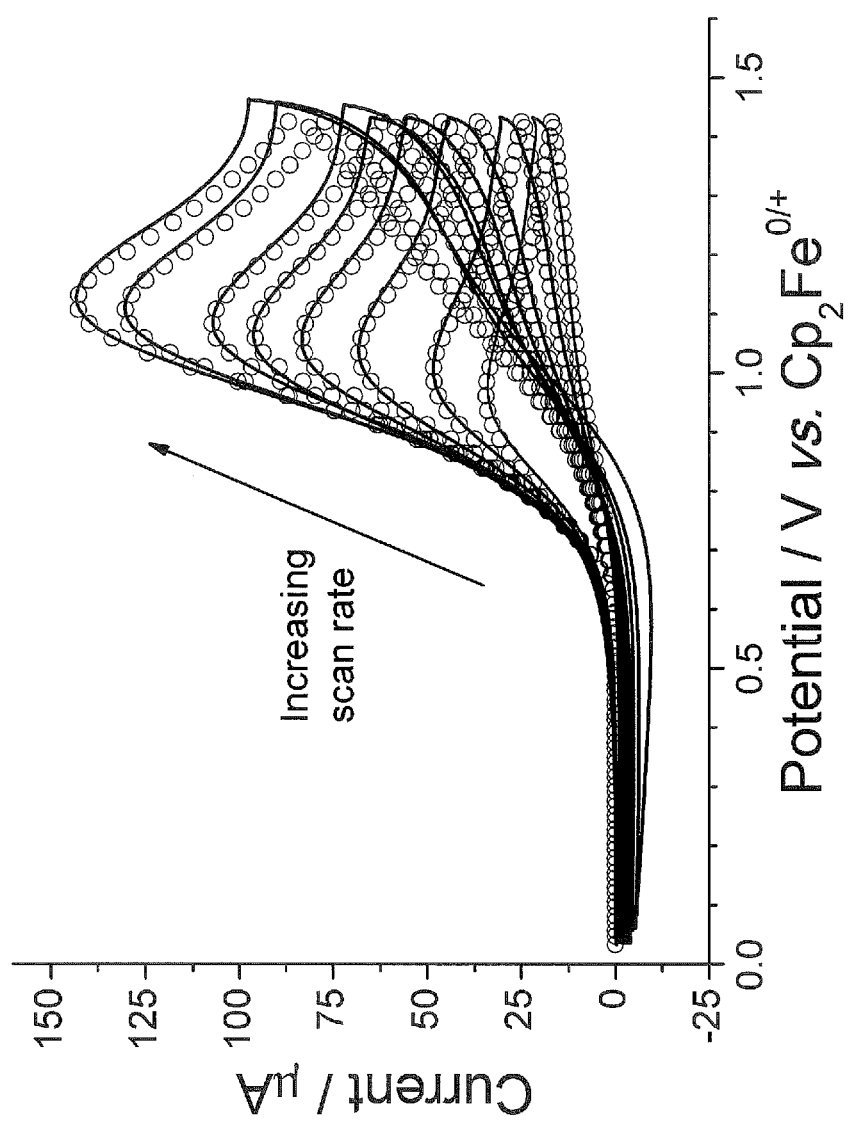
FIG. 5 is a series of cyclic voltammograms showing the oxidation of a specific aromatically substituted borohydride.

FIG. 5 shows cyclic voltammograms of a 4.9 mM solution of [$^{n}$Bu$_4$N][HB(C$_6$F$_5$)$_3$] in CH$_2$Cl$_2$ recorded at voltage scan rates of 50, 100, 200, 300, 400, 500, 750, and 1000 mVs$^{-1}$ on a glassy carbon electrode (GCE). Solid lines are experimental data; open circles are best fit simulated data (see Examples)

FIG. 6 shows a cyclic voltammogram of a 5 mM solution of $^{t}$Bu$_3$P and B(C$_6$F$_5$)$_3$ in CH$_2$Cl$_2$ solution, at a GCE, after being exposed to a 1 hour sparge with H$_2$ (black line). Addition of authentic [$^{n}$Bu$_4$N]1 (dotted line) to the sample confirms that the observed oxidation wave corresponds to the H$_2$-activated product. The cyclic voltammograms were taken in the presence of a Cp$_2$Fe internal reference at a voltage scan rate of 100 mV s$^{-1}$.

FIG. 7 shows the cyclic voltammetry of a saturated solution of H$_2$ containing 2.3 mM Cp$_2$Fe$^{0/+}$ as internal reference in CH$_2$Cl$_2$ recorded at a voltage scan rate of 100 mVs$^{-1}$.

Figure 9:
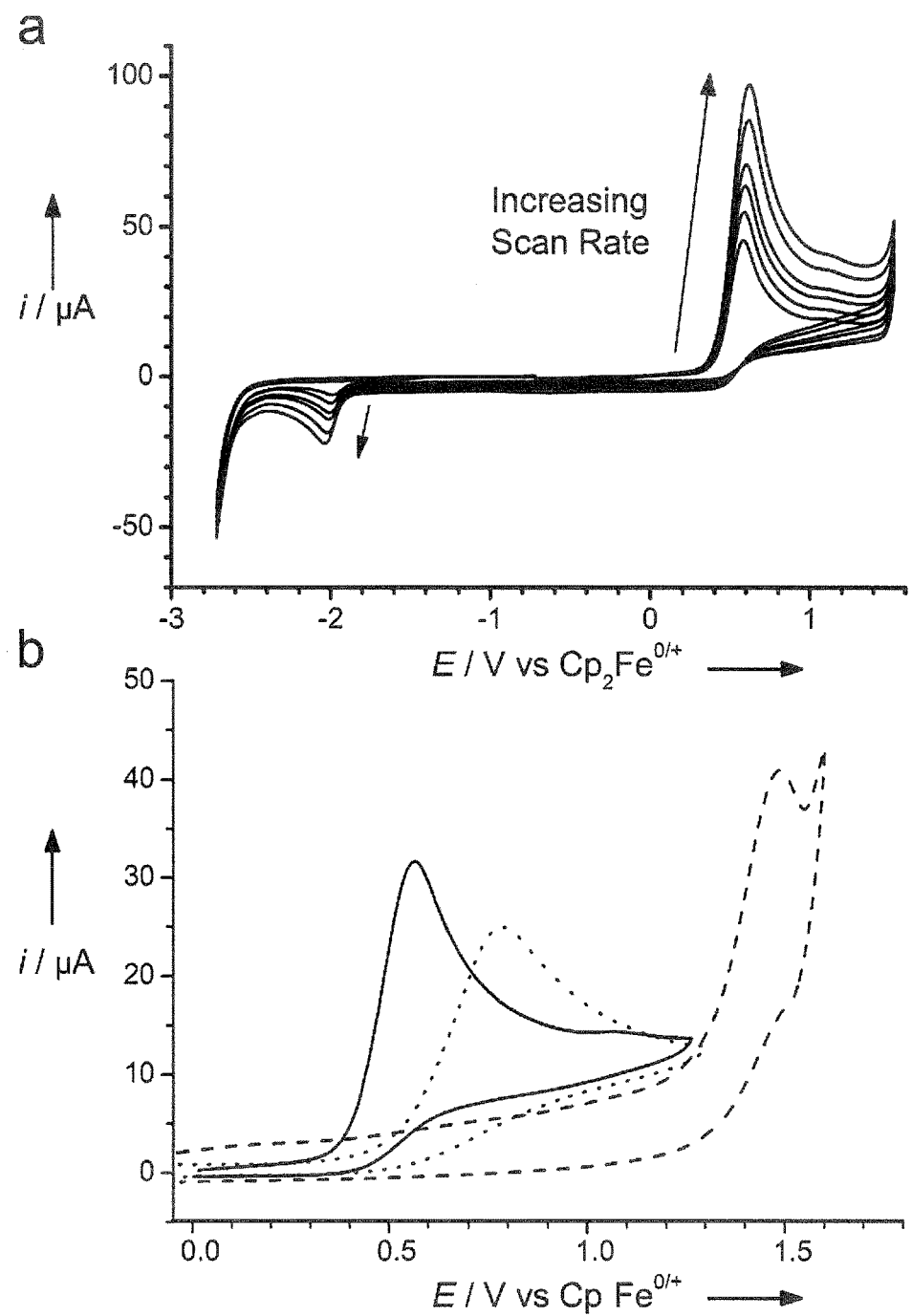
FIG. 9 is a set of graphs showing the oxidation of a specific N-heterocyclic carbene (NHC) stabilised borenium cation Lewis acid, (N,N-($^{i}$Pr)imidazole-2-ylidene)(9-borabicylco[3.3.1]nonane).

FIG. 9 shows (a) Overlaid cyclic voltammograms showing the full potential window for the NHC-9BBN borohydride adduct (1) from Scheme (IV) (2.0 mM, CH$_2$Cl$_2$) over the voltage scan rate range 200-1000 mV s$^{-1}$; and (b) Cyclic voltammograms comparing the oxidation potentials of (1) from Scheme (IV) (solid line, 2.0 mM), [HB(C$_6$F$_6$)$_3$]$^-$ (dotted line, 2.0 mM), H$_2$ (dashed line, saturated solution) in CH$_2$Cl$_2$ at voltage scan rates of 100 mV s$^{-1}$.

Figure 10:
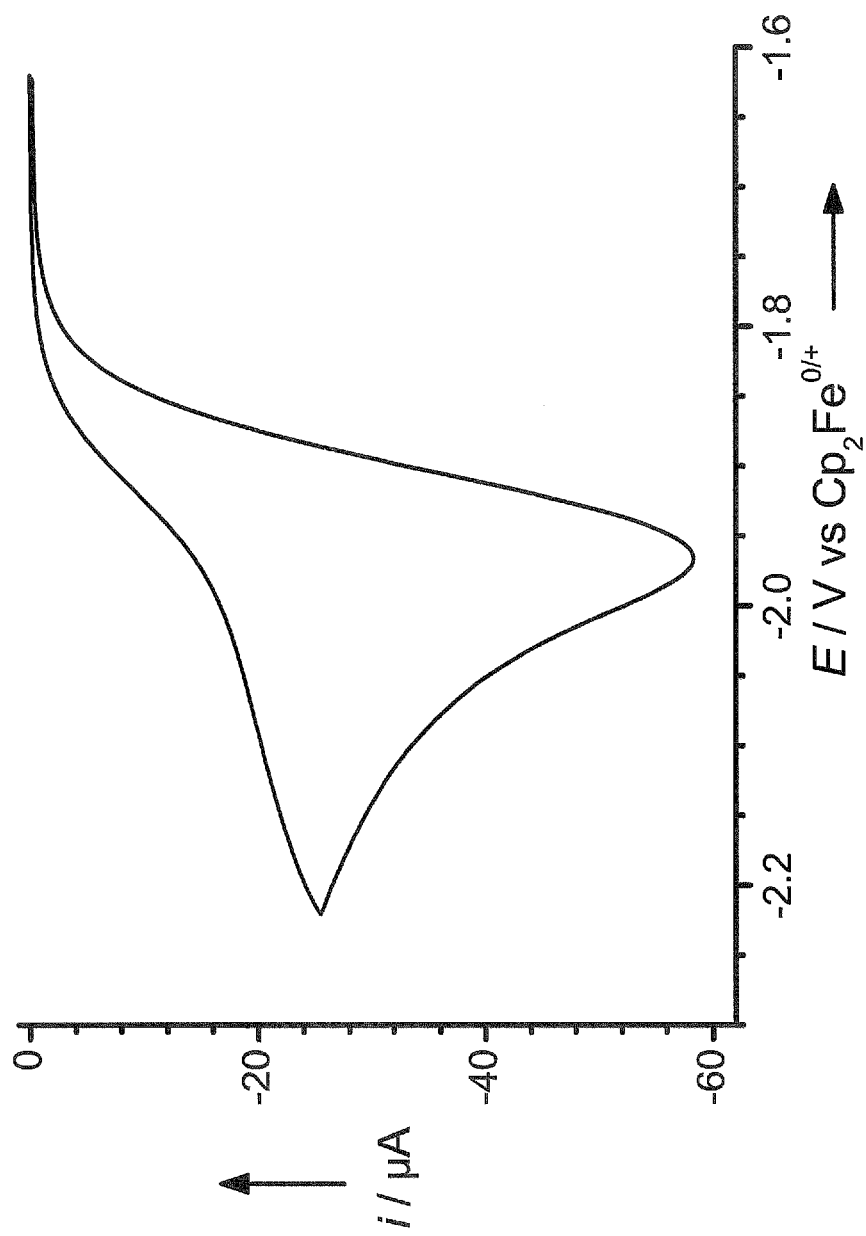
FIG. 10 is a cyclic voltammogram showing the reduction of a specific N-heterocyclic carbene (NHC) stabilised borenium cation Lewis acid.

FIG. 10 shows a cyclic voltammogram showing the reduction of authentic 2[B(C$_6$F$_5$)$_4$] from Scheme (IV) (4.3 mM, CH$_2$Cl$_2$) at a voltage scan rate of 100 mV s$^{-1}$.

Figure 11:
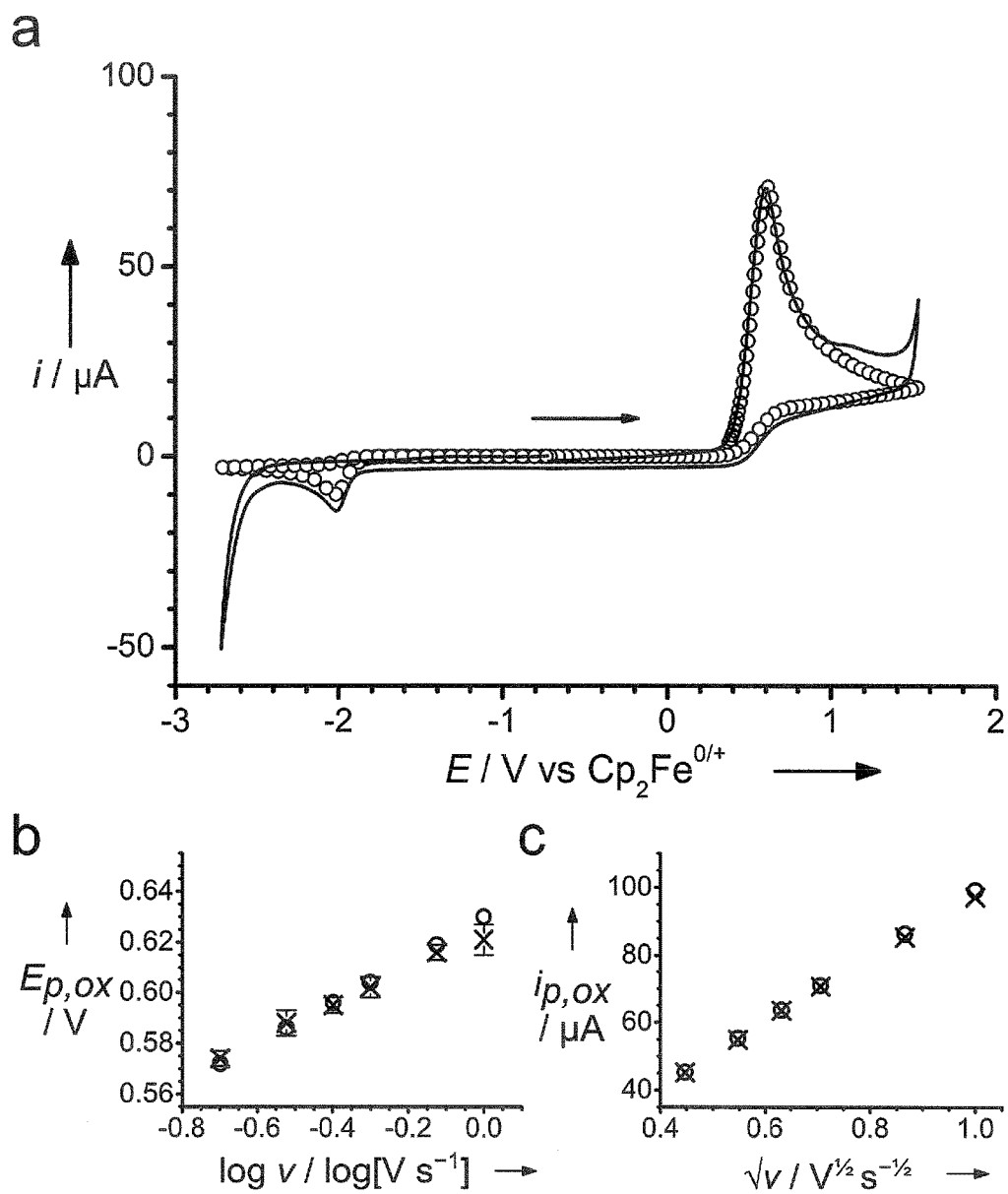
FIG. 11 is a set of graphs; (a) showing the oxidation of a specific N-heterocyclic carbene (NHC) stabilised borenium cation Lewis acid, (N,N-($^{i}$Pr)imidazole-2-ylidene)(9-borabicylco[3.3.1]nonane).

FIG. 11 shows (a) Simulated (circles) and experimental (line) cyclic voltammograms showing the full potential window for (1) from Scheme (IV) (2.0 mM, CH$_2$Cl$_2$) at a voltage scan rate (v) of 500 mV s$^{-1}$; Comparisons between experimental and simulated data showing the quality of fitting for: and (b) the oxidative peak potential (E$_{p,\ ox}$) vs the logarithm of voltage scan rate (v); c) the oxidative peak current (i$_{p,\ ox}$) vs the square root of voltage scan rate (v).

EXAMPLES

The following examples are provided for illustrative purposes to describe the invention in more detail.

Example 1: 610 mV Reduction in Overpotential for the Oxidation of H$_2$ Using B(C$_6$F$_5$)$_3$ Electrocatalytic Frustrated Lewis Pairs Methods:

Commercially available reagents were purchased from Sigma-Aldrich (Gillingham, UK) and used without further purification unless stated otherwise. All synthetic reactions and manipulations were performed under a rigorously dry N$_2$ atmosphere (BOC Gases) using standard Schlenk-line techniques on a dual manifold vacuum/inert gas line or either a Saffron or MBraun glovebox. All glassware was flame-dried under vacuum before use. Anhydrous solvents were dried via distillation over appropriate drying agents. All solvents were sparged with nitrogen gas to remove any trace of dissolved oxygen and stored in ampules over activated 4 Å molecular sieves. $^n$Bu$_4$NCl and NOPF$_6$ were purchased from Alfa Aesar. $^n$Bu$_4$NCl was recrystallized from acetone prior to use. H$_2$ gas (99.995%) was purchased from BOC gases and passed through drying columns containing P$_4$O$_{10}$ and 4 Å molecular sieves. D$_2$ gas was generated in situ from the reaction of Na with degassed D$_2$O (99.9%, Cambridge Isotope Laboratories Inc.); it was passed through a drying column containing P$_4$O$_{10}$. Deuterated NMR solvents ([D$_6$]DMSO, 99.9%; CDCl3, 99.8%; C$_6$D$_6$, 99.5%) were purchased from Cambridge Isotope Laboratories Inc. and were dried over P$_4$O$_{10}$, degassed using a triple freeze-pump-thaw cycle and stored over activated 4 Å molecular sieves. B(C$_6$F$_5$)$_3$, [$^n$Bu$_4$N][B(C$_6$F$_5$)$_4$], [H(OEt$_2$)$_2$][B(C$_6$F$_5$)$_4$] and $^t$Bu$_3$P were prepared according to literature methods (S. J. Lancaster. Alkylation of boron trifluoride with pentafluorophenyl Grignard reagent; Tris(pentafluorophenyl)boron; borane. *ChemSpider SyntheticPages* 2003. http://cssp.chemspider.com/215. DOI: 10.1039/SP215; Martin, E.; Hughes, D. L.; Lancaster, S. *J. Inorg. Chim. Acta* 2010, 363, 275-278; LeSuer, R. J.; Buttolph, C.; Geiger, W. E. *Anal. Chem.* 2004, 76, 6395-6401; Jutzi, P.; Müller, C.; Stammler, A.; Stammler, H.-G. *Organometallics* 2000, 19, 1442-1444; Srivastava, R. C. *J. Chem. Res.* (S) 1985, 330-331.). [TMPD][DB(C$_6$F$_5$)$_3$] was prepared using an adapted literature method (Sumerin, V.; Schulz, F.; Nieger, M.; Leskela, M.; Repo, T.; Rieger, B. *Angew. Chem. Int. Ed.* 2008, 47, 6001-6003.). Synthesis and characterization of compounds [$^n$Bu$_4$N][HB(C$_6$F$_5$)$_3$] and [$^n$Bu$_4$N][DB(C$_6$F$_5$)$_3$] are detailed below (vide infra).

NMR spectra were recorded using either a Bruker Avance DPX-300 MHz or Bruker Avance DPX-500 MHz spectrometer. Chemical shifts are reported in ppm and are referenced relative to appropriate standards: $^{19}$F (CFCl$_3$); $^{11}$B (Et$_2$O.BF$_3$), $^{31}$P (85% H$_3$PO$_4$). Sample headspace analysis was performed using a Perkin Elmer Clarus 580 gas chromatograph coupled with a thermal conductivity detector (GC-TCD). Retention time for H$_2$ gas was calibrated using a standard sample.

All electrochemical experiments were performed using either an Autolab PGSTAT 30 or PGSTAT 302N computer-controlled potentiostat. Cyclic voltammetry (CV) was performed using a three-electrode configuration consisting of a glassy carbon macrodisk working electrode (GCE) (nominal diameter of 3 mm; BASi, Indiana, USA) combined with a Pt wire counter electrode (99.99%; GoodFellow, Cambridge, UK) and a Ag wire pseudoreference electrode (99.99%; GoodFellow, Cambridge, UK). The GCE was polished between experiments using successive grades of diamond paste slurries from 3.0 to 0.1 µm (Kemet, Maidstone, UK). The electrodes were briefly sonicated in distilled water and rinsed with ethanol between each polishing step, to remove any adhered microparticles. The electrodes were then dried in an oven at 100° C. to remove any residual traces of water. The GCE electroactive area was calibrated for each experiment using a 5 mM ferrocene solution in CH$_3$CN solvent containing 0.1 M [$^n$Bu$_4$N][PF$_6$] as the supporting electrolyte. The electroactive area was accurately determined by construction of a Randles-Sevcik plot from cyclic voltammograms recorded at varying scan rates (50-750 mVs$^{-1}$). The Ag wire pseudoreference electrodes were calibrated to the ferrocene/ferrocenium couple in CH$_2$Cl$_2$ at the end of each run to allow for any drift in potential, following IUPAC recommendations. Controlled potential bulk electrolysis was performed using a three-electrode configuration consisting of a carbon felt (99.0%; Alfa Aesar, Massachusetts, USA) working electrode combined with a Ag wire pseudo-reference electrode (99.99%, GoodFellow, Cambridge, UK) and a Pt gauze counter electrode (52 mesh woven from 0.1 mm diameter wire, 99.9%; Alfa Aesar, Massachusetts, USA). The working and pseudo-reference electrodes were separated from the counter electrode compartment by a porous glass frit. All electrochemical measurements were performed at ambient temperatures under an inert N$_2$ atmosphere in CH$_2$Cl$_2$ containing 0.05-0.10 M [$^n$Bu$_4$N][B(C$_6$F$_5$)$_4$] as the supporting electrolyte. All electrochemical measurements were iR-compensated to within 80±5% of the solution uncompensated resistance.

Digital simulation of voltammetric data was performed using the commercially available DigiElch™ Pro software package (v.7).

Synthesis and Characterisation

Na[HB(C$_6$F$_5$)$_3$]

To a solution of 1.0 M Na[HBEt$_3$] in toluene (3.7 mL, 3.7 mmol) was added a solution of B(C$_6$F$_5$)$_3$ (1.71 g, 3.3 mmol) in toluene (30 mL). The reaction mixture was left to stir under N$_2$ at room temperature for 2 h, during which time a white precipitate formed. The precipitate was left to settle before it was filtered and triturated with toluene (2×10 mL). The residue was dried in vacuo to yield Na[HB(C$_6$F$_5$)$_3$] (1.15 g, 2.1 mmol) as a fine white powder in 64% yield. $^1$H NMR (300 MHz, [D$_6$]DMSO): δ 3.56 (br. q, J=87 Hz, 1H); $^{19}$F NMR (282 MHz, [D$_6$]DMSO): δ −132.9 (m, 6F, ortho-F), −162.8 (m, 3F, para-F), −166.1 (m, 6F, meta-F); $^{11}$B NMR (96.3 MHz, [D$_6$]DMSO): δ −25.2 ppm (d, J=87 Hz); $^{13}$C NMR (75.5 MHz, [D$_6$]DMSO): δ 147.5 (dm, J=236 Hz, ortho-C), 137.2 (dm, J=243 Hz, para-C), 135.8 (dm, J=246 Hz, meta-C), 124.9 (s, ipso-C).

[$^n$Bu$_4$N][HB(C$_6$F$_5$)$_3$]

A solution of $^n$Bu$_4$NCl (0.45 g, 1.6 mmol) in CH$_2$Cl$_2$ (20 mL) was added to a white suspension of Na[HB(C$_6$F$_5$)$_3$] (0.86 g, 1.6 mmol) in CH$_2$Cl$_2$ (20 mL) at room temperature, with stirring under N$_2$. This resulted in the formation of a fine flocculent precipitate with the simultaneous breakup of the suspended material. The reaction mixture was left to stir overnight. The precipitate was then allowed to settle before it was filtered. The filtrate was concentrated in vacuo until a minimum quantity of solvent remained. A white precipitate was obtained at room temperature by layering the solution carefully with light petroleum ether (40/60, approximately twice the volume of solution was added). The precipitate was filtered and dried in vacuo to afford [$^n$Bu$_4$N][HB(C$_6$F$_5$)$_3$] (0.89 g, 1.2 mmol) as a white powder in 74% yield. Crystals suitable for X-ray crystallography (colourless plates) were grown by dissolving [$^n$Bu$_4$N][HB(C$_6$F$_5$)$_3$] in a minimum quantity of CH$_2$Cl$_2$, warming to ca. 35° C., adding an equal quantity of light petroleum ether and slow-cooling to room temperature. $^1$H NMR (300 MHz, CDCl$_3$): δ 3.60 (br. q, J=82 Hz, 1H, BH), 3.07 (m, 8H, CH$_2$), 1.56 (m, 8H, CH$_2$), 1.32 (m, 8H, CH$_2$), 0.92 (t, J=7.2 Hz, 12H, CH$_3$); $^{19}$F NMR (282 MHz, CDCl$_3$): δ −133.6 (m, 6F, ortho-F), −163.4 (m, 3F, para-F), −166.7 (m, 6F, meta-F); $^{11}$B NMR (96.3 MHz, CDCl$_3$): δ −25.4 (d, J=82 Hz); $^{13}$C NMR (75.5 MHz, CDCl$_3$): δ 148.3 (dm, J=240 Hz), 138.0 (dm, J=245 Hz), 136.6 (dm, J=248 Hz), 125.0, 58.9, 23.8, 19.6, 13.4.

[TMPD][DB(C$_6$F$_5$)$_3$]

A clear yellow solution of 2,2,6,6-tetramethylpiperidine (TMP) (0.28 g, 1.95 mmol) in toluene (10 mL) was added to a clear colourless solution of B(C$_6$F$_5$)$_3$ (1.00 g, 1.95 mmol) in toluene (20 mL) to give a clear, pale yellow solution. The sample was sparged with $D_2$ gas for 1 h. The pale yellow solution was then concentrated to ca. 5 mL and pentane (15 mL) was added to give a precipitate. The precipitate was allowed to settle and then filtered to give [TMPD][DB($C_6F_5$)$_3$] (1.15 g, 1.75 mmol) as a white powder in 90% yield. $^1$H NMR (500 MHz, $C_6D_6$): δ 4.23 (t, J=49 Hz, 1H, NH), 0.76 (m, 2H, $CH_2$), 0.67 (m, 4H, $CH_2$) 0.56 (s, 12H, $CH_3$); $^{19}$F NMR (471 MHz, $C_6D_6$): δ −133.1 (m, 6F, ortho-F), −161.7 (m, 3F, para-F), −165.5 (m, 6F, meta-F); $^{11}$B NMR (160 MHz, $C_6D_6$): δ −23.8 (s); $^2$D NMR (556 MHz, $CH_2Cl_2$): δ 5.40 (d, J=1.1 Hz, ND), 3.60 (br. m, BD).

[$^n$Bu$_4$N][DB($C_6F_5$)$_3$]

A clear colourless solution of [TMPD][DB($C_6F_5$)$_3$] (0.31 g, 0.47 mmol) in toluene (20 mL) was added to NaH (11 mg, 0.47 mmol) to give some effervescence. The reaction mixture was left to stir at room temperature under $N_2$ overnight. The reaction mixture was then filtered and the filtrate was concentrated in vacuo. The residue was dissolved in $CH_2Cl_2$ (10 mL) to give a clear colourless solution. To this was added a clear colourless solution of N$^n$Bu$_4$Cl (0.13 g, 0.47 mmol) in $CH_2Cl_2$ (10 mL). A very fine precipitate rapidly formed. The reaction mixture was left to stir at room temperature for 1 h before it was filtered. The filtrate was concentrated to ca. 2 mL to give a white precipitate. This was filtered and the filtrated was concentrated in vacuo to yield a colorless viscous oil that solidified overnight to give [$^n$Bu$_4$N][DB($C_6F_5$)$_3$] (0.10 g, 0.13 mmol) as an amorphous colorless solid in 28% yield. $^{19}$F NMR (471 MHz, CDCl$_3$): δ −133.5 (m, 6F, ortho-F), −163.4 (m, 3F, para-F), −166.6 (m, 6F, meta-F); $^{11}$B NMR (160 MHz, CDCl$_3$): δ −25.3 (d, J=82 Hz). $^2$D NMR (556 MHz, $CH_2Cl_2$): δ 3.66 (br. s).

Results and Discussion

Initial Electrochemical Studies.

An authentic sample of [$^n$Bu$_4$N][HB($C_6F_5$)$_3$], containing the hydridic component ([HB($C_6F_5$)$_3$]$^−$) of the FLP $H_2$-cleavage step, was prepared and its structure established by X-ray crystallography and spectroscopic methods. This allowed a detailed electrochemical study into the redox behaviour of [HB($C_6F_5$)$_3$]$^−$ to be undertaken. The direct voltammetric oxidation of [$^n$Bu$_4$N] [HB($C_6F_5$)$_3$], at varying concentrations, was performed at a macrodisk glassy carbon electrode (GCE) using cyclic voltammetry (FIGS. 4 and 5).

A weakly coordinating electrolyte system comprising 0.05 M [$^n$Bu$_4$N][B($C_6F_5$)$_4$] in $CH_2Cl_2$ was selected for all electrochemical studies to preclude the decomposition of B($C_6F_5$)$_3$ (as taught in Ashley, A. E.; Herrington, T. J.; Wildgoose, G. G.; Zaher, H.; Thompson, A. L.; Rees, N. H.; Kramer, T.; O'Hare, D. *J. Am. Chem. Soc.* 2011, 133, 14727-14740.) On sweeping the potential anodically at a scan rate of 100 mV s$^{−1}$, an oxidative wave was initially observed with a peak potential of ($E_p$) +0.88±0.01 V vs Cp$_2$Fe$^{0/+}$, and no corresponding (quasi-reversible) reduction peak was observed upon reversing the scan direction. However, a small irreversible reduction wave was observed at 1.59 V vs Cp$_2$Fe$^{0/+}$ ( ) that we assign to the reduction of some catalytically regenerated parent Lewis acid, B($C_6F_5$)$_3$ from our previous studies (Lawrence, E. J.; Oganesyan, V. S.; Wildgoose, G. G.; Ashley, A. E. *Dalton Trans.* 2013, 42, 782-789.) The small size of this reduction wave is likely as a result of subsequent protonolysis of the parent B($C_6F_5$)$_3$ (see Scheme (III) below). The observed voltammetry can be explained by the mechanism proposed in Scheme (III), which is supported by excellent fit between simulation and experiment (FIGS. 4 and 5) and detailed chemical and density functional theory (DFT) studies described below. The globally optimized parameters describing the oxidation of [HB($C_6F_5$)$_3$] were obtained from digital simulation of the CVs and are given in Table 1, whilst the parameters describing the reduction of B($C_6F_5$)$_3$ are taken from our previous work (Lawrence, E. J.; Oganesyan, V. S.; Wildgoose, G. G.; Ashley, A. E. *Dalton Trans.* 2013, 42, 782-789.).

Scheme (III). Proposed mechanism and associated thermodynamic and kinetic parameters used in simulation of the voltammetric oxidation of {HB($C_6F_5$)$_3$]$^−$ at a GCE. (standard reduction potential, $E^0$ / V; standnrard electron transfer rate constant, $k^0$ / cm s$^{-1}$; chemical rate constant, k / s$^{-1}$).

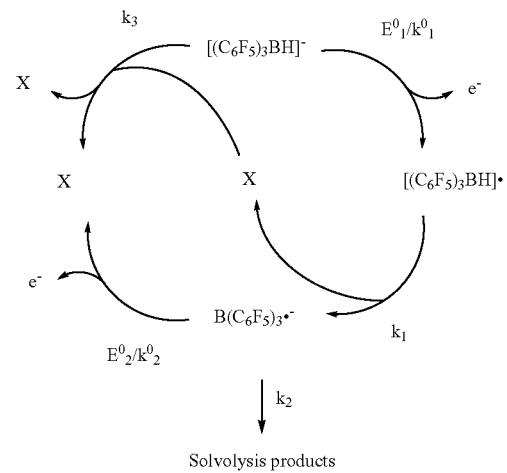

TABLE 1

Globally optimized best-fit thermodynamic and kinetic parameters obtained from digital simulation of voltammetric data for [$^n$Bu$_4$N][HB($C_6F_5$)$_3$] at a GCE, following the mechanism proposed in Scheme (III). For clarity the [HB($C_6F_5$)$_3$]$^-$ and [HB($C_6F_5$)$_3$]$^•$ species are denoted in this table as 1$^-$ and 1$^•$ respectively

| | Redox Parameters | | |
|---|---|---|---|
| Redox Process | $E^0$/V vs Cp$_2$Fe$^{0/+}$ | $k^0/10^{-3}$ cm s$^{-1}$ | Charge transfer coefficient α |
| 1$^-$ ⇌ 1$^•$ + e$^-$ | +1.13 ± 0.05 | 13 ± 2 | 0.74 ± 0.1 |
| B($C_6F_5$)$_3$$^{•-}$ ⇌ B($C_6F_5$)$_3$ + e$^-$ | −1.79 ± 0.01$^a$ | 1.3 ± 0.3$^a$ | 0.50 ± 0.05$^a$ |

| Chemical Step | Rate Constant k |
|---|---|
| 1$^•$ → B($C_6F_5$)$_3$$^{•-}$ + H$^+$ | $k_1 > 1 \times 10^{13}$ s$^{-1}$ |
| B($C_6F_5$)$_3$$^{•-}$ → Solvolysis | $k_2 > 6.1$ s$^{-1a}$ |
| 1$^-$ + H$^+$ → B($C_6F_5$)$_3$ + H$_2$ | $k_3 = 1.50 ± 0.25 \times 10^7$ M$^{-1}$s$^{-1}$ |

$^a$Parameters taken from our previous studies of B($C_6F_5$)$_3$ (Lawrence, E. J.; Oganesyan, V. S.; Wildgoose, G. G.; Ashley, A. E. *Dalton Trans.* 2013, 42, 782-789.).

Chemical Studies.

When [$^n$Bu$_4$N][HB($C_6F_5$)$_3$] is subjected to chemical oxidation using a stoichiometric amount of the single-electron oxidant [NO][PF$_6$] in $CH_2Cl_2$, effervescence is observed. Analysis of the reaction mixture headspace using gas chromatography with a thermal conductivity detector (GC-TCD) found that $H_2$ gas was evolved. Two mechanisms for $H_2$ production are possible: i) the reaction of electrogenerated H$^+$ with the parent [HB($C_6F_5$)$_3$]$^-$ as we propose (Scheme (III)), or ii) by the recombination of H$^•$ radicals that are released from the transient [(C$_6$F$_5$)$_3$BH]$^•$ intermediate. In order to exclude the possibility of the latter pathway, we conducted a control experiment using an authentic source of H$^•$, $^n$Bu$_3$SnH, which was mixed with 4-bromobenzophenone in equimolar quantities in a sealed NMR tube and allowed to react under UV light. $^1$H-NMR characterization of the products revealed the formation of benzophenone via the radical dehalogenation of 4-bromobenzophenone by FL However, when [$^n$Bu$_4$N][HB(C$_6$F$_5$)$_3$] is stoichiometrically oxidized in the presence of [NO][PF$_6$] and an equimolar amount of 4-bromobenzophenone, the latter is recovered in quantitative yield by NMR; no benzophenone is detected in the reaction mixture. Furthermore, effervescence is observed when [$^n$Bu$_4$N][HB(C$_6$F$_5$)$_3$] and a stoichiometric amount of Jutzi's strong oxonium acid, [H(OEt$_2$)$_2$][B(C$_6$F$_5$)$_4$], are combined in CH$_2$Cl$_2$. H$_2$ gas is once again detected in the reaction headspace, supporting the proposed proton-mediated H$_2$ evolution mechanism. Note that in either case $^{11}$B-NMR characterization of the product mixture reveals a number of peaks in the range 0.5 to 7.0 ppm consistent with our previous characterization (Lawrence, E. J.; Oganesyan, V. S.; Wildgoose, G. G.; Ashley, A. E. *Dalton Trans.* 2013, 42, 782-789.) of solvolysis products of B(C$_6$F$_5$)$_3$.$^-$ and F$^-$ abstraction products from the [PF$_6$]$^-$ anion in the former case (see below).

Conclusively, when a sample of deuterated [$^n$Bu$_4$N][DB (C$_6$F$_5$)$_3$] is subjected to bulk electrolytic oxidation at a glassy carbon electrode in the presence of $^t$Bu$_3$P, an intense triplet resonance is seen in the $^{31}$P{$^1$H} NMR spectrum at 59.6 ppm (J=65.8 Hz), which corresponds to [$^t$Bu$_3$P-D]$^+$. Since the only possible source of D$^+$ is from the oxidation of [DB(C$_6$F$_5$)$_3$]$^-$, this strongly supports the proposed mechanism in Scheme (III), wherein B—D/B—H bond cleavage in [DB(C$_6$F$_5$)$_3$]. results in the formation of a deuteron/proton, respectively.

DFT Calculations.

Computational modeling of the HOMO and LUMO of the geometry optimized [HB(C$_6$F$_5$)$_3$]$^-$ species and the SOMO of the [HB(C$_6$F$_5$)$_3$]. intermediate lends further support to our mechanism. Interestingly, partial charge calculations for [HB(C$_6$F$_5$)$_3$]$^-$ reveal that the B—H bond is not particularly polar, as verified by the computed partial charges on the atoms (−0.099 and +0.078 on H and B respectively); this indicates that [HB(C$_6$F$_5$)$_3$]$^-$ is a weak hydride donor, and is consistent with the results of previous studies involving the FLP reduction of small molecules.[41,42] The B—C and B—H bond dissociation energies for the [HB(C$_6$F$_5$)$_3$]$^-$ were calculated as $\Delta H_{B-C}$=408.1 kJmol$^{-1}$ and $\Delta H_{B-H}$=312.2 kJmol$^{-1}$ respectively, whilst for [HB(C$_6$F$_5$)$_3$]. the values were found to be $\Delta H_{B-C}$=71.7 kJmol$^{-1}$ and $\Delta H_{B-H}$=34.0 kJmol$^{-1}$ respectively. This indicates that the electrochemical oxidation of [HB(C$_6$F$_5$)$_3$]$^-$ strongly facilitates B—H bond cleavage. The spin density of the SOMO is predominantly located in the B—H bond, whose strength in the radical intermediate is almost comparable to a hydrogen bonding interaction between B(C$_6$F$_5$)$_3$.$^-$ and H$^+$.[43] Note that these are gas phase DFT calculations; it is likely that heterolytic cleavage of the B—H bond in [HB(C$_6$F$_5$)$_3$]$^-$ to produce charged ions (Scheme (III)) is energetically favorable in the solution phase and rapid, as determined from our digital simulations of the redox process.

In Situ Electrochemical FLP Experiments.

With a detailed understanding of the redox chemistry of [HB(C$_6$F$_5$)$_3$]$^-$ we proceeded towards in situ electrochemical studies of the archetypal $^t$Bu$_3$P/B(C$_6$F$_5$)$_3$ system during the FLP cleavage of H$_2$. The H$_2$ FLP reaction was complete after 12 hours when monitored by $^1$H, $^{31}$P, $^{19}$F and $^{11}$B-NMR methods, but even within 1 hour there is evidence of cleavage.

FIG. 6 shows the resulting voltammetry recorded after a 1:1 solution of $^t$Bu$_3$P:B(C$_6$F$_5$)$_3$ (containing ferrocene as an internal reference) was sparged with H$_2$ gas for 1 hour. Reassuringly, we observe the characteristic oxidation wave of [HB(C$_6$F$_5$)$_3$]$^-$, which is identical to that of [$^n$Bu$_4$N][HB (C$_6$F$_5$)$_3$]. Confirmation of this was shown by a proportional increase in the oxidation current at +0.88 V vs Cp$_2$Fe$^{0/+}$ when the solution was spiked with an authentic sample of [$^n$Bu$_4$N][HB(C$_6$F$_5$)$_3$] (FIG. 6). H$_2$ is itself oxidized sluggishly, with a broad, ill-defined wave at ca. +1.49 V vs. Cp$_2$Fe$^{0/+}$ in CH$_2$Cl$_2$ on a glassy carbon electrode (see FIG. 7). Hence, by employing combined electrochemical FLP approach the oxidation of H$_2$ now occurs with a ca. 610 mV (117.7 kJ mol$^{-1}$) reduction in the required driving force. Note that [$^t$Bu$_3$PH]$^+$ is not redox active at the potentials studied. However, some oxidation of unreacted $^t$Bu$_3$P is apparent as a small oxidation wave at +0.44 V vs Cp$_2$Fe$^{0/+}$.

Example 2: 910 mV Reduction in Overpotential for the Oxidation of H$_2$ Using N-Heterocyclic Carbene (NHC) Stabilized Borenium Cation [(I$^i$Pr$_2$)(BC$_8$H$_{14}$)]$^+$, Derived from 9-Borabicyclo[3.3.1] Nonane (9-BBN) in an Electrocatalytic Frustrated Lewis Pair Methods:

The same general methods as described above in Example 1 were repeated for this example.

Synthesis and Characterization:

For the purposes of this example the species concerned are labelled as 1 and 2 as denoted in Scheme (IV) below.

Scheme (IV) Electrooxidation of the H$_2$-activated $^t$Bu$_3$P/[B(C$_6$F$_5$)$_4$]2 frustrated Lewis pair (FLP) results in the electrochemical generation of two protons and two electrons.

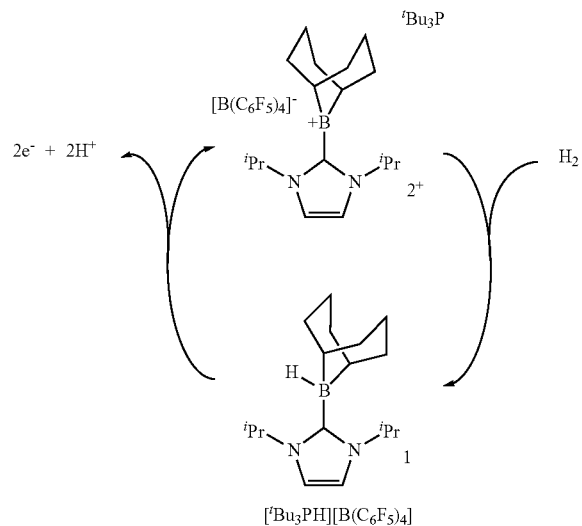

Synthesis of NHC-9BBN (1):

The NHC-9BBN borohydride adduct (1) was prepared from the combination of 1,3-diisopropylimidazol-2-ylidene with the 9-BBN dimer according to the literature method of Farrell et. al. (J. M. Farrell, J. A. Hatnean, D. W. Stephan, *J. Am. Chem. Soc.* 2012, 134, 15728-15731.). Scheme (V) below shows the Proton-mediated generation of 2[B(C$_6$F$_5$)$_4$] from The NHC-9BBN borohydride adduct (1).

Scheme (V): Proton-mediated generation of 2[B(C$_6$F$_5$)$_4$] from (1).

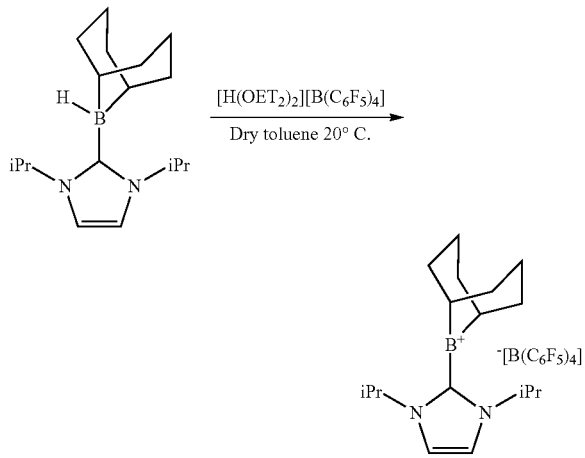

To a solution of 1 (0.14 g, 0.53 mmol) in toluene (5 mL) was added a suspension of [H(OEt$_2$)$_2$][B(C$_6$F$_5$)$_4$] (0.41 g, 0.53 mmol) in toluene (10 mL). Vigorous effervescence was immediately observed and a gelatinous precipitate was formed. The reaction mixture was left to stir overnight before it was concentrated in vacuo to give a white powder. The residue was recrystallized from chlorobenzene (3 mL) overnight at −20° C. The crystals were then filtered and washed with dry petrol (4×1 mL). The crystals were dried in vacuo to yield 2[B(C$_6$F$_5$)$_4$] (0.42 g, 0.41 mmol, 77%) as a white powder. $^1$H NMR (300 MHz, CDCl$_3$): δ=7.61 (s, 2H), 4.77 (m, $^3$J (H,H)=6.8 Hz, 2H; CH), 2.44-2.24 (br. m, 6H), 2.20-2.12 (br. m, 2H) 2.10-1.94 (br. m, 4H), 1.88-1.59 (br. m, 2H), 1.68 (d, $^3$J (H,H)=6.7 Hz, 12H; CH$_3$); $^{19}$F NMR (471 MHz, CDCl$_3$): δ=−137.7 (m, 8F; ortho-F), −168.2 (m, 4F; para-F), −172.1 (m, 8F; meta-F); $^{11}$B NMR (160 MHz, CDCl$_3$): δ=83.8 (br), −16.7 (s).

Results and Discussion

Electrochemical Characterisation:

Electrochemical characterisation of an authentic sample of the borohydride, 1, was undertaken using cyclic voltammetry. On scanning a solution of 1 from the open-circuit potential (the resting/equilibrium potential where no current flows) to more positive potentials, a single oxidation wave was observed at +0.58±0.01 V vs Cp$_2$Fe$^{0/+}$ (see FIG. 9) with no corresponding reduction wave observed at scan rates up to 5 Vs$^{-1}$. If the reverse scan is extended in a reductive (negative) direction then a smaller, irreversible reduction wave is observed at −1.97±0.01 V vs Cp$_2$Fe$^{0/+}$ which we attribute to the reduction of 2$^+$ formed by the oxidation of 1 (see FIG. 9).

Indeed, as shown in FIG. 9(b), the observed voltammetry for the electrooxidation of 1 is similar in its behavior to that shown in Example 1 above using [HB(C$_6$F$_5$)$_3$]$^-$ and thus we propose the mechanism shown in Scheme (VI) to account for the observed voltammetry: upon the application of an oxidizing potential 1 undergoes a one-electron oxidation to form a transient 1•$^+$ species. This undergoes rapid dissociation in solution to form a proton and a neutral radical, 2• As the applied potential is very much larger than the formal potential for the 2$^+$/2• couple (see below), this radical undergoes a second one-electron oxidation to generate 2$^+$. This second oxidation is in competition with solvolytic decomposition of the neutral radical. Another competing process is the reaction between electrogenerated H$^+$ and an incoming parent 1 to generate 2$^+$ and H$_2$. Whilst this reduces the overall efficiency of the Lewis acid catalyzed oxidation of H$_2$, the hydrogen can be subsequently recycled (see below). The net oxidation current is therefore intermediate between that expected for a single-electron and two-electron oxidation.

Scheme (VI). The proposed mechanism and associated thermodynamic and kinetic parameters used in digital simulation of the voltammetric oxidation of 1 at a GCE.

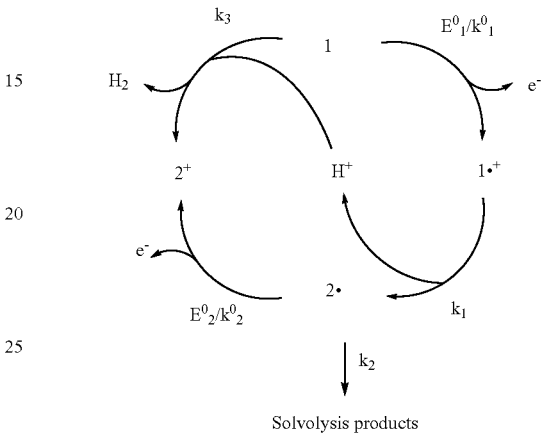

The reduction wave observed at 1.97 V vs. Cp$_2$Fe$^{0/+}$ is due to the one-electron reduction of 2$^+$. This was independently confirmed by performing cyclic voltammetry on an authentic sample of 2[B(C$_6$F$_5$)$_4$], prepared according to literature methods (J. M. Farrell, J. A. Hatnean, D. W. Stephan, *J. Am. Chem. Soc.* 2012, 134, 15728-15731.), whereupon the same irreversible reduction wave is observed (see FIG. 10).

The reduction of 2$^+$ to form 2• is irreversible at all scan rates up to 5 Vs$^{-1}$ due to rapid solvolysis of 2• to form redox inactive, four-coordinate borate species, analogous to the reduction of B(C$_6$F$_5$)$_3$ (Lawrence, E. J.; Oganesyan, V. S.; Wildgoose, G. G.; Ashley, A. E. *Dalton Trans.* 2013, 42, 782-789.) The reduction wave corresponding to 2$^+$, generated during the oxidation of 1, is much larger than that observed for the parent Lewis acid following the electrooxidation of [HB(C$_6$F$_5$)$_3$]$^-$ shown in Example 1 above. The protolytic side-reaction between electrogenerated H$^+$ and 1 was confirmed by treating a sample of 1 with one equivalent of Jutzi's strong acid, [H(OEt)$_2$][B(C$_6$F$_5$)$_4$], whereupon effervescence was immediately observed. $^{11}$B and $^1$H NMR spectroscopy gave evidence for the quantitative conversion of 1 to 2[B(C$_6$F$_5$)$_4$]. Note this is in stark contrast to the protonolysis of [HB(C$_6$F$_5$)$_3$]$^-$ using Jutz's acid, where neither the free Lewis acid, B(C$_6$F$_5$)$_3$, or the etherate adduct, Et$_2$O.B(C$_6$F$_5$)$_3$, were found to be present. Instead protolytic decomposition of the parent, B(C$_6$F$_5$)$_3$ Lewis acid was found to occur, producing two $^{11}$B NMR signals characteristic of four-coordinate boron species.[38] This chemical result, together with the observation of a significant reduction peak in the voltammetry of 1 (corresponding to significant amounts of 2$^+$ formed), indicates that replacing a borohydride, [HB(C$_6$F$_5$)$_3$]$^-$ with the NHC-9-BBN adduct, 1, markedly improves the stability of the parent Lewis acid towards protolysis.

Digital simulation of the cyclic voltammetric data for the oxidation of 1 was undertaken in order to extract pertinent mechanistic, thermodynamic and kinetic parameters. The postulated ECE mechanism in Scheme (IV) was applied to baseline-corrected and iR-compensated cyclic voltammograms of 1, taken over a scan rate range of 200-1000 mV s$^{-1}$. Any non-Faradaic current, resulting from double-layer capacitance, was not accounted for in the simulations. The electrochemical parameters for the reduction of electrogenerated 2$^+$ were determined by separate fits to the voltammetric data obtained for the reduction of 2[B(C$_6$F$_5$)$_4$] with an EC mechanism over the same range of voltage scan rates. The experimental and simulated cyclic voltammograms were found to be in excellent agreement (FIG. 11) when simulated according to the proposed ECE mechanism in Scheme (VI).

The heterogeneous electrochemical parameters: formal potential, $E°_f$, standard electron transfer rate constant, $k°$, and charge transfer coefficient, $\alpha$, are listed in Table 2, together with rate constants, $k_1$-$k_3$, for the associated homogeneous chemical follow-up reactions.

TABLE 2

Globally optimized best-fit thermodynamic and kinetic parameters for the oxidation of 1 at a GCE, obtained from digital simulation of the voltammetric data following the proposed mechanism in Scheme (IV).

| Redox process | $E°/V$ vs $Cp_2Fe^{0/+}$ | $k°/cm\ s^{-1}$ | $\alpha$ |
|---|---|---|---|
| 1 ⇌ 1$^{•+}$ + e$^-$ | +0.736 ± 0.01 | 4.0 ± 0.1 × 10$^{-1}$ | 0.5 |
| 2$^{•}$ ⇌ 2$^+$ + e$^-$ | −1.935 ± 0.01 | 3.4 ± 0.1 × 10$^{-3}$ | 0.6 |

| Chemical step | Rate constant, k |
|---|---|
| 1$^{•+}$ → 2$^{•}$ + H$^+$ | $k_1 > 3.0 \times 10^{11}$ M$^{-1}$s$^{-1}$ |
| 2$^{•}$ → Solvolysis | $k_2 > 2 \times 10^{13}$ s$^{-1}$ |
| 1 + H$^+$ → 2$^+$ + H$_2$ | $k_3 = 50$ s$^{-1}$ |

Comparing the results of our digital simulations for the 1/2$^+$ system to those obtained for the analogous [HB(C$_6$F$_5$)$_3$]$^-$/B(C$_6$F$_5$)$_3$ system that we reported previously,[38] three observations are apparent: i) the rate of oxidation of 1 is ca. forty times greater than for [HB(C$_6$F$_5$)$_3$]$^-$, leading to larger oxidative currents (see FIG. 9(b)), significant for any potential energy applications of such a system. Furthermore this oxidation occurs at potentials ca. 300 mV lower than for [HB(C$_6$F$_5$)$_3$]−corresponding to a very large reduction in the required overpotential of −910 mV (equivalent to a 269.8 kJmol$^{-1}$ reduction in energetic driving force) for the direct, non-aqueous oxidation of H$_2$ at a glassy carbon electrode (see FIG. 9(b)); ii) the rate of unwanted protonation of 1 by electrogenerated H$^+$ to generate 2$^+$ and H$_2$ (k$_3$) is 3×10$^5$ times slower than in the [HB(C$_6$F$_5$)$_3$]$^-$ system. This, combined with the resistance of 1/2$^+$ to protolytic decomposition (as evidenced by quantitative recovery of 2$^+$ when 1 is treated with Jutzi's strong acid, described above), demonstrates a significant improvement in using borenium cations in place of electron deficient boranes in these electrochemical FLP systems; iii) The relative magnitudes of k$_1$-k$_3$ vs the exponentially potential-dependent rate of electron transfer determines the concentration of 2$^+$ at any given point during a cyclic voltammetry experiment. Digital simulations reveal that whilst 2$^+$ is generated through two pathways (the desired oxidation of the transient 2$^•$ radical and the undesired protonation of incoming 1 by electrogenerated H$^+$) only 30-40% of the concentration of 2$^+$ reduced at the electrode surface is formed from the protonation of incoming 1. This is a marked improvement over the [HB(C$_6$F$_5$)$_3$]$^-$/B(C$_6$F$_5$)$_3$ system, shown in Example 1 above.

The invention claimed is:

1. A method of electrocatalytically oxidizing dihydrogen (H$_2$) using a Lewis acid, a Lewis base and at least one electrode; the method comprising the steps of:
   a. introducing the dihydrogen to the Lewis acid and the Lewis base; and
   b. heterolytically cleaving the dihydrogen to produce an electrochemically active Lewis acid hydride; and
   c. electrochemically oxidizing the electrochemically active Lewis acid hydride,
   wherein the Lewis acid and Lewis base are a frustrated Lewis pair;
   wherein the Lewis acid is in accordance with Formula (I):

Formula (I)

wherein:
   A is a Group 13 element capable of behaving as a Lewis acid;
   M$_1$ and M$_2$ are each independently selected from carbocyclyl, hydrocarbyl or heterocyclyl, each of which is optionally substituted with at least one substituent selected from cyano, halo, hydroxyl, nitro, mesityl, substituted mesityl, (C$_{1-6}$)alkyl, (C$_{3-6}$)cycloalkyl, (C$_{1-6}$)alkoxy, phenyl, (C$_{1-6}$)alkylphenyl, heterocyclyl, (C$_{1-6}$)alkylheterocyclyl, or a linker group which is capable of binding the A atom to a solid support; and
   M$_3$ is selected from hydrogen, halo, any one of the groups defined above for M$_1$ or M$_2$ or a linker group which is capable of binding the A atom to a solid support,
   wherein the Lewis base is an oxygen containing compound of the general Formula (III):

Formula (III)

wherein:
   R$^{21}$ and R$^{22}$ are each independently selected from hydrogen, hydrocarbyl, carbocyclyl, heterocyclyl, each of the hydrocarbyl, carbocyclyl, and heterocyclyl groups is optionally substituted with amino, aryl, cyano, halo, heterocyclyl, nitro, (C$_{1-6}$)alkyl or (C$_{1-6}$)alkoxy; or
   R$^{21}$ and R$^{22}$ are coupled so that they form a four, five, six or seven atom, saturated or unsaturated ring, which may optionally comprise one or two additional heteroatoms selected from nitrogen, oxygen or sulphur, and optionally substituted with one or more substituent groups selected from amino, cyano, halo, nitro, trifluoromethyl, (C$_{1-6}$)alkoxy, or —S(O)$_r$—(C$_{1-6}$)alkyl (where r represents zero, one or two).

2. The method according to claim 1, wherein the Lewis acid and/or the Lewis base is immobilized on the surface of the at least one electrode.

3. The method according to claim 1, wherein A is boron.

4. The method according to claim 1, wherein
   M$_1$ and M$_2$ are each independently selected from a mesityl or a substituted mesityl; and
   M$_3$ is hydrogen.

5. The method according to claim 4, wherein
M$_1$ and M$_2$ are each independently selected from 2,6-(CH$_3$)$_2$(C$_6$H$_3$), 3,5-(CH$_3$)$_2$(C$_6$H$_3$) or 3,5-(CF$_3$)$_2$(C$_6$H$_3$); and
M$_3$ is hydrogen.

6. The method according to claim 1, wherein the Lewis acid is a compound in accordance with Formula (II):

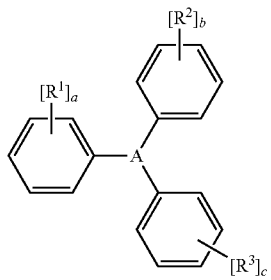

Formula (II)

wherein:
R$^1$, R$^2$ and R$^3$ are each independently selected from amino, cyano, halo, hydroxy, nitro, phenyl, (C$_{1-6}$)alkyl, (C$_{3-6}$)cycloalkyl, (C$_{1-6}$)alkoxy, (C$_{1-6}$)alkylphenyl;
a is selected from zero, one, two, three, four or five;
b is selected from zero, one, two, three, four or five; and
c is selected from zero, one, two, three, four or five.

7. The method according to claim 6, wherein R$^1$, R$^2$ and R$^3$ are each independently selected from fluoro, chloro or cyano.

8. The method according to claim 1, wherein the Lewis acid is B(C$_6$F$_5$)$_3$, B(C$_6$Cl$_5$)$_3$, B(C$_6$F$_5$)(C$_6$Cl$_5$)$_2$, B(C$_6$F$_5$)$_2$(C$_6$Cl$_5$), Al(C$_6$F$_5$)$_3$, B(C$_6$F$_4$H)$_3$, BCl(C$_6$F$_5$)$_2$, [HB(C$_6$F$_5$)$_2$]$_n$ where n is 1 or 2, B(2,6-(CH$_3$)$_2$(C$_6$H$_3$))$_3$, B(3,5-(CH$_3$)$_2$(C$_6$H$_3$))$_3$, BH(3,5-(CF$_3$)$_2$(C$_6$H$_3$))$_3$, BH(2,6-(CH$_3$)$_2$(C$_6$H$_3$))$_2$, BH(3,5-(CH$_3$)$_2$(C$_6$H$_3$))$_2$, BH(3,5-(CF$_3$)$_2$(C$_6$H$_3$))$_2$ or B(C$_6$CL$_4$F)$_3$.

9. The method according to claim 1, wherein the Lewis acid is stabilised cationic complexes of the structure of Formula (Ia) shown below:

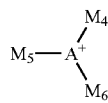

Formula (Ia)

where:
A$^+$ is a Group 13 ion capable of behaving as a Lewis acid, such as B$^+$ or Al$^+$;
M$_4$ and M$_5$ are each independently selected from carbocyclyl, hydrocarbyl fluorocarbyl, chlorocarbyl, chloro-fluorocarbyl, fluoro-hydrocarbyl, chloro-hydrocarbyl or heterocyclyl, each of which is optionally substituted with at least one substituent selected from cyano, halo, hydroxyl, nitro, mesityl, substituted mesityl, (C$_{1-6}$)alkyl, (C$_{3-6}$)cycloalkyl, (C$_{1-6}$)alkoxy, phenyl, (C$_{1-6}$)alkylphenyl, heterocyclyl, (C$_{1-6}$)alkylheterocyclyl, SO$_2$aryl, SO$_2$alkyl, or M$_4$ and M$_5$ are coupled so that they form a four, five, six or seven, eight, nine, or ten atom, saturated or unsaturated, mono- or bicyclic ring, which may optionally comprise one or two additional heteroatoms selected from nitrogen, oxygen or sulphur, and optionally substituted with one or more substituent groups selected from amino, cyano, halo, nitro, trifluoromethyl, (C$_{1-6}$)alkyl, (C$_{1-6}$)alkoxy, or —S(O)$_r$—(C$_{1-6}$)alkyl (where r represents zero, one or two), or a linker group which is capable of binding the A atom to a solid support; and
M$_6$ is an electron pair donor ligand coordinated A$^+$.

10. The method according to claim 9, wherein A$^+$ is a boron cation.

11. The method according to claim 9, wherein M$_6$ is a phosphine or a carbene.

12. The method according to claim 11, wherein the Lewis acid is an N-heterocyclic carbene stabilized borenium Lewis acid in accordance with Formula (IIa):

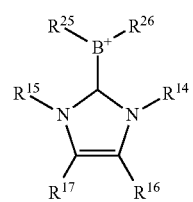

Formula (IIa)

wherein:
R$^{14}$ and R$^{15}$ are selected from hydrogen or (C$_{1-6}$)alkyl,
R$^{16}$ and R$^{17}$ are both selected from amino, cyano, halo, hydrogen, nitro, trifluoromethyl, (C$_{1-6}$)alkyl, (C$_{1-6}$)alkoxy, NH(C$_{1-6}$)alkyl, N[(C$_{1-6}$)alkyl]$_2$, —S(O)$_r$—(C$_{1-6}$)alkyl (where r represents zero, one or two) or aryl; or
any one of R$^{14}$, R$^{15}$, R$^{16}$ and R$^{17}$ is a linker that links the Lewis base to a solid support; and
R$^{25}$ and R$^{26}$ are each independently selected from carbocyclyl, hydrocarbyl or heterocyclyl, each of which is optionally substituted with at least one substituent selected from cyano, halo, hydroxyl, nitro, mesityl, substituted mesityl, (C$_{1-6}$)alkyl, (C$_{3-6}$)cycloalkyl, (C$_{1-6}$)alkoxy, phenyl, (C$_{1-6}$)alkylphenyl, heterocyclyl, (C$_{1-6}$)alkylheterocyclyl.

13. The method according to claim 12, wherein R$^{14}$ and R$^{15}$ are each independently a (C$_{1-6}$)alkyl; R$^{16}$ and R$^{17}$ are hydrogen or halo; and R$^{21}$ and R$^{22}$ are each independently selected from hydrocarbyl, fluorocarbyl, chlorocarbyl, chloro-fluorocarbyl, fluoro-hydrocarbyl, chloro-hydrocarbyl phenyl or mesityl, each of which is optionally substituted with at least one substituent selected from fluoro, chloro or cyano.

14. The method according to claim 12, wherein R$^{14}$ and R$^{15}$ are each independently selected from methyl, ethyl, n-propyl, isopropyl, n-butyl, sec-butyl or tert-butyl; and R$^{25}$ and R$^{26}$ represent a 9 borabicyclo[3.3.1]nonane bridge or each of R$^{25}$ and R$^{26}$ can independently be a C$_6$F$_5$, C$_6$Cl$_5$, 2,6-(CH$_3$)$_2$(C$_6$H$_3$), 3,5-(CH$_3$)$_2$(C$_6$H$_3$) or 3,5-(CF$_3$)$_2$(C$_6$H$_3$).

15. The method according to claim 12, wherein the Lewis acid is selected from [($^i$Pr$_2$—NHC)(B(2,6-(CH$_3$)$_2$C$_6$H$_3$)$_2$)]$^+$, [($^i$Pr$_2$—NHC)(B(3,5-(CH$_3$)$_2$C$_6$H$_3$)$_2$)]$^+$ or [($^i$Pr$_2$—NHC)(B(3,5-(CF$_3$)$_2$C$_6$H$_3$)$_2$)]$^+$.

16. The method according to claim 1, wherein the Lewis base is THF.

17. The method according to claim 1, wherein the Lewis base is water.

* * * * *